US008772569B2

(12) United States Patent
Schneider et al.

(10) Patent No.: US 8,772,569 B2
(45) Date of Patent: Jul. 8, 2014

(54) EDGE FOLD HAVING SUBSTANTIALLY UNIFORM GATHERS FOR ABSORBENT ARTICLE AND METHOD FOR MAKING

(75) Inventors: Uwe Schneider, Mason, OH (US); Christoph Schmitz, Euskirchen (DE); Adi Jackels, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 914 days.

(21) Appl. No.: 12/046,752

(22) Filed: Mar. 12, 2008

(65) Prior Publication Data

US 2008/0215025 A1    Sep. 4, 2008

Related U.S. Application Data

(62) Division of application No. 10/665,949, filed on Sep. 18, 2003, now Pat. No. 7,368,027.

(51) Int. Cl.
| | | |
|---|---|---|
| *A61F 13/15* | (2006.01) | |
| *A61F 13/20* | (2006.01) | |
| *A61F 13/45* | (2006.01) | |
| *A61F 13/56* | (2006.01) | |

(52) U.S. Cl.
CPC ............... *A61F 13/20* (2013.01); *A61F 13/56* (2013.01)
USPC ............... 604/365; 604/385.16; 604/385.24; 604/385.25

(58) Field of Classification Search
USPC ............... 604/385.16, 385.24–385.3, 365
See application file for complete search history.

(56) References Cited

U.S. PATENT DOCUMENTS

| | | | |
|---|---|---|---|
| 3,509,881 A | 5/1970 | Sabee | |
| 3,860,003 A | 1/1975 | Buell et al. | |
| 4,381,781 A | 5/1983 | Sciaraffa et al. | |
| 4,397,704 A | 8/1983 | Frick | |
| 4,515,595 A | 5/1985 | Kievit et al. | |
| 4,695,278 A | 9/1987 | Lawson | |
| 4,704,115 A * | 11/1987 | Buell | 604/385.26 |
| 4,710,189 A | 12/1987 | Lash | |
| 4,795,454 A | 1/1989 | Dragoo | |
| 4,808,178 A | 2/1989 | Aziz et al. | |

(Continued)

FOREIGN PATENT DOCUMENTS

| | | |
|---|---|---|
| EP | 0 844 062 A1 | 5/1998 |
| EP | 0 955 027 A1 | 11/1999 |
| WO | WO 95/16746 A1 | 6/1995 |

OTHER PUBLICATIONS

U.S. Appl. No. 08/115,048, filed Nov. 19, 1993, Robles, et al.

*Primary Examiner* — Tatyana Zalukaeva
*Assistant Examiner* — Benedict L Hanrahan
(74) *Attorney, Agent, or Firm* — Chuck R. Ware; Amy M. Foust; Abbey A. Lopez

(57) ABSTRACT

An absorbent article may have an edge fold having substantially uniform gathers. The edge fold may form a finished edge cuff. The finished edge cuff may be formed around and/or along a portion of a longitudinal edge. The edge fold may be formed by folding and seaming existing material (i.e., without the addition of a discrete part). The edge fold may be extensible, or elastic. The edge fold may completely encircle the portion of the longitudinal edge that defines the leg opening of a diaper. A method and an apparatus for forming an edge fold are also provided.

13 Claims, 28 Drawing Sheets

(56) References Cited

U.S. PATENT DOCUMENTS

| | | |
|---|---|---|
| 4,816,025 A | 3/1989 | Foreman |
| 4,857,067 A | 8/1989 | Wood et al. |
| 4,909,803 A | 3/1990 | Aziz et al. |
| 4,938,753 A | 7/1990 | Van Gompel et al. |
| 4,968,313 A | 11/1990 | Sabee |
| 5,026,364 A | 6/1991 | Robertson |
| 5,143,679 A | 9/1992 | Weber et al. |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,518,801 A | 5/1996 | Chappell et al. |
| 5,527,304 A | 6/1996 | Buell et al. |
| 5,536,350 A | 7/1996 | Klemp |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,155 A | 1/1997 | Nishikawa et al. |
| 5,607,537 A | 3/1997 | Johnson et al. |
| 5,607,760 A | 3/1997 | Roe |
| 5,609,587 A | 3/1997 | Roe |
| 5,628,741 A | 5/1997 | Buell et al. |
| 5,635,191 A | 6/1997 | Roe et al. |
| 5,643,588 A | 7/1997 | Roe et al. |
| 5,662,638 A | 9/1997 | Johnson et al. |
| 5,669,897 A | 9/1997 | LaVon et al. |
| 5,674,216 A | 10/1997 | Buell et al. |
| 5,685,874 A | 11/1997 | Buell et al. |
| 5,730,738 A * | 3/1998 | McFall et al. .................. 604/387 |
| 5,730,821 A | 3/1998 | Joest et al. |
| 5,776,121 A | 7/1998 | Roe et al. |
| 5,779,691 A | 7/1998 | Schmitt |
| 5,810,800 A * | 9/1998 | Hunter et al. ............. 604/385.23 |
| 5,865,823 A | 2/1999 | Curro |
| 5,899,895 A | 5/1999 | Robles et al. |
| 5,914,084 A | 6/1999 | Benson et al. |
| 6,114,263 A | 9/2000 | Benson et al. |
| 6,120,632 A | 9/2000 | Dragoo et al. |
| 6,500,377 B1 | 12/2002 | Schneider et al. |
| 6,605,172 B1 | 8/2003 | Anderson et al. |
| 6,764,478 B2 * | 7/2004 | Ashton et al. ............. 604/385.25 |
| 7,368,027 B2 * | 5/2008 | Schneider et al. ............. 156/226 |
| 2002/0087139 A1 | 7/2002 | Popp et al. |
| 2003/0004488 A1 | 1/2003 | Ashton et al. |
| 2003/0004489 A1 | 1/2003 | Ashton et al. |
| 2003/0088227 A1 | 5/2003 | Schneider et al. |
| 2004/0044322 A1 | 3/2004 | Melius |

\* cited by examiner

EDGE FOLD HAVING SUBSTANTIALLY UNIFORM GATHERS FOR ABSORBENT ARTICLE AND METHOD FOR MAKING

CROSS REFERENCE TO RELATED APPLICATION

This application is a divisional of U.S. application Ser. No. 10/665,949, filed Sep. 18, 2003, now U.S. Pat. No. 7,368,027, the substance of which is incorporated herein by reference.

FIELD OF THE INVENTION

This invention relates to edge folds on absorbent articles, and more particularly to edge folds having substantially uniform gathers on disposable absorbent articles, such as diapers.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art.

A typical absorbent article has a chassis that includes a liquid pervious topsheet, and a liquid impervious backsheet joined to the topsheet. An absorbent core is typically positioned between the topsheet and the backsheet. The chassis has a generally elongated shape, which can be rectangular or hourglass shaped. The long dimension of the chassis defines two opposed edges referred to as the longitudinal edges. A portion of each longitudinal edge defines the leg opening of the diaper when worn.

To better contain body exudates, absorbent articles often have elasticized leg openings, referred to as leg cuffs that are designed to fit snugly about the legs of the wearer. Leg cuffs can be made by simply placing tensioned elastic strands along the longitudinal edges, for example. When contracted the elastic strands form gathers of material. Leg cuffs, as opposed to barrier cuffs that are generally disposed inboard, that is, toward the center of the diaper and away from the longitudinal edges of the diaper chassis, can include a portion of the longitudinal edge of the diaper chassis. This longitudinal edge is often unsightly, that is, it appears as an unfinished edge that may have a rather rough appearance. The appearance is important, as consumer perception of softness and comfort are significant considerations for commercial success in the disposable absorbent article field.

It would be desirable to have a disposable absorbent article having a leg cuff that has a finished, comfortable appearance.

Additionally, it would be desirable to have a method for making a leg cuff having a finished appearance in a commercially viable manner.

Further, it would be desirable to have a disposable absorbent article with a leg cuff having a finished appearance, with the finished appearance limited to the portion of the longitudinal edge of the chassis that defines a leg opening when worn. Said finished appearance being formed by an edge fold having substantially uniform gathers.

Finally, it would be desirable to have a commercially-viable method of making a disposable absorbent article with a leg cuff having a finished appearance, with the finished appearance limited to the portion of the longitudinal edge of the chassis that defines a leg opening when worn. Said finished appearance being formed by an edge fold having substantially uniform gathers.

BRIEF SUMMARY OF THE INVENTION

In some aspects, the invention relates to an absorbent article comprising a leg elastic and a chassis with a longitudinal edge that includes a leg opening portion with a leg opening portion length. At least a portion of the chassis adjacent to the leg opening portion may be an activated portion. The activated portion may be incrementally stretched along an activated portion length. The activated portion may have an overall shape that is substantially arched. The leg elastic may be disposed along at least a portion of the activated portion. At least a portion of the activated portion may be a folded portion. The folded portion may be folded laterally inward along a folded portion length. At least a portion of the folded portion may be bonded along a bonded portion length inboard to the leg elastic, forming an edge fold. The edge fold may completely encircle at least the bonded portion length of the longitudinal edge that defines the leg opening. The edge fold may have substantially uniform gathers.

The leg opening portion may be substantially parallel to a longitudinal centerline of the article. Substantially all of the leg opening portion may be curved. The chassis may include a first waist region and a second waist region. The leg opening portion may extend over substantially all of a distance between the first waist region and the second waist region. The activated portion may extend over substantially all of the leg opening portion length. The folded portion may extend along substantially all of the activated portion length. The bonded portion may extend along substantially all of the folded portion length. The edge fold may have an overall shape that is substantially curved. The bond may be selected from the group including an adhesive bond, an ultrasonic bond, a compression bond, a thermal bond, a radio frequency bond, an infrared bond, and combinations thereof. The absorbent article may be disposable, or wearable, and may be selected from the group including disposable diapers, sanitary napkins, pantiliners, incontinence briefs, and incontinence undergarments. The absorbent article may further comprise a barrier leg cuff.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIGS. 13A-C show a progression of the folding step, wherein, FIG. 13A shows the longitudinal edge being held by folding portion in a pre-folded state, FIG. 13B shows the folding portion folding the longitudinal edge to create an edge fold, FIG. 13C shows the folding portion releasing the newly-formed edge fold;

DETAILED DESCRIPTION OF THE INVENTION

Figure 1:
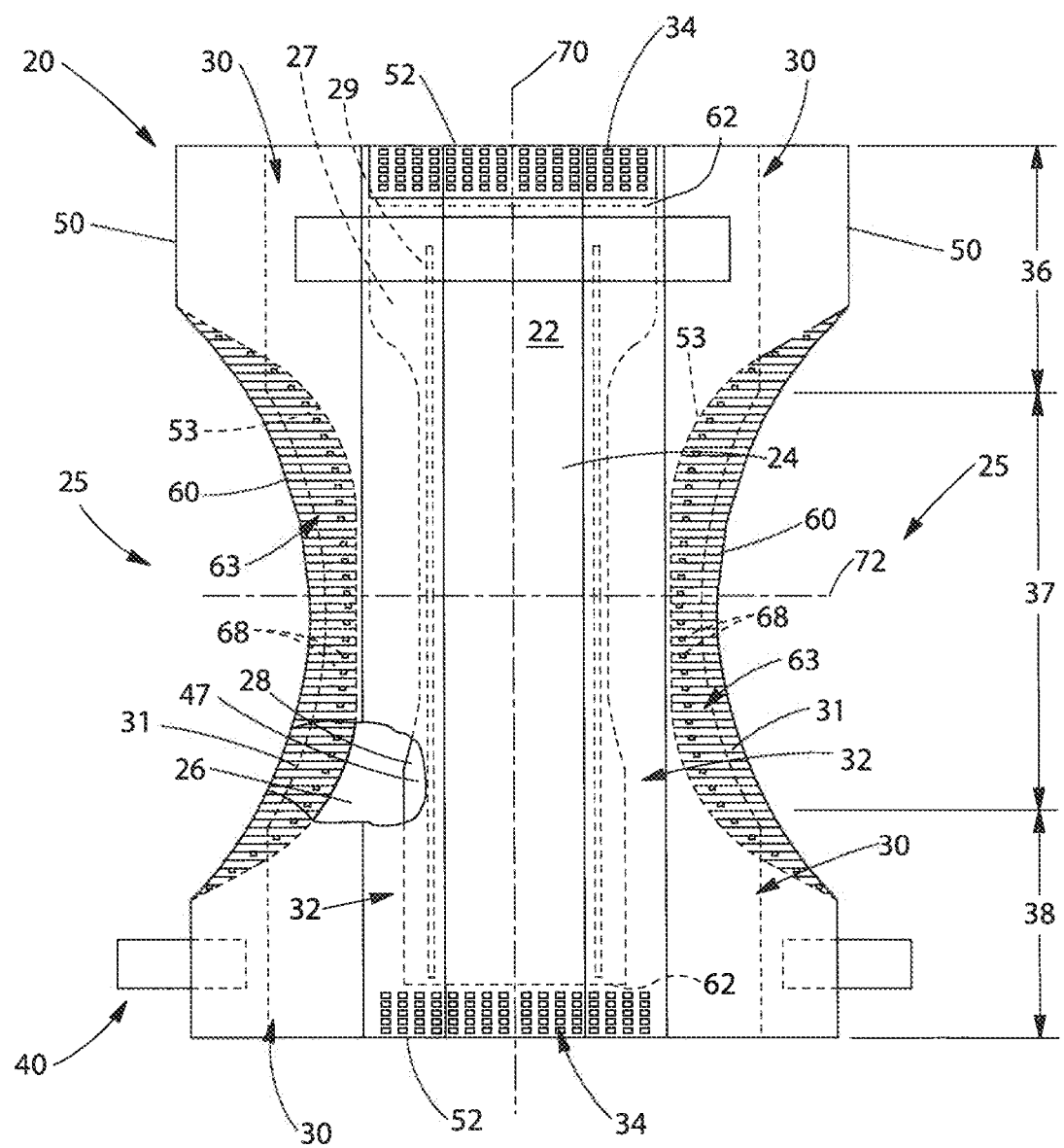
FIG. 1 is a perspective view of a general embodiment of an absorbent article of the present invention with a partial cutaway.

As used herein, the term "absorbent article" refers to devices that absorb and contain body exudates, and more specifically, refers to devices that are placed against or in proximity to the body of the wearer to absorb and contain the various exudates discharged from the body. Absorbent articles include, but are not limited to, disposable diapers, sanitary napkins, pantiliners, incontinence briefs, and incontinence undergarments. The term "disposable" is used herein to describe absorbent articles that generally are not intended to be laundered or otherwise restored or reused as an absorbent article (i.e., they are intended to be discarded after a single use).

As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) that in turn are affixed to the other element.

As used herein, the term "elastic" or "elastomeric" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1.0) cm sample of a material which is elongatable to at least 1.60 cm, and which, upon being elongated to 1.60 cm and released, will recover to a length of not more than 1.27 cm. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are referred to herein as "highly elastic".

As used herein, the term "nonelastic" refers to any material that does not fall within the definition of "elastic" (or "elastomeric") or "highly elastic" above.

As used herein, the term "extensible" refers to any material that, upon application of a biasing force, is elongatable, at least about 50% without offering a significant resistance force (less than 10 g/cm) or experiencing catastrophic failure. Catastrophic failure includes substantial tearing, fracturing, rupturing, or other failure in tension such that, if tested in a standard tensile tester, the failure would result in a sudden significant reduction in measured tensile force. As used herein, the term "highly extensible" refers to any material which, upon application of a biasing force, is elongatable, at least about 70%, more preferably at least about 100%, and even more preferably about 120% without offering a significant resistance force (less than 10 g/cm) or experiencing catastrophic failure.

As used herein, the term "diaper" refers to an absorbent article generally worn by infants and incontinent persons about the lower torso, and includes both tape-type diapers (diapers having adhesive tapes, hook and loop fasteners, and the like, that fastened about the waist of the wearer), and pull-on pant-type diapers.

As used herein, the term "multi-piece chassis" refers to a chassis having attached side panels. In contrast, the term "uni-body chassis" refers to a chassis having integral side panels and having a final shape determined by a side notch cut.

FIG. 1 is a plan view of the diaper 20 of the present invention in a flat-out state with portions of the structure being cut away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26, an absorbent core 28 which is preferably positioned between at least a portion of the topsheet 24 and the backsheet 26; side panels 30; elasticized leg cuffs 32; and an elastic waist feature 34.

Diaper 20 is shown in FIG. 1 to have a first waist region 36, a second waist region 38 opposed to the first waist region 36 and a crotch region 37 located between the first waist region and the second waist region 38. Crotch region 37 preferably being narrower than first waist region 36 and second waist region 38. The periphery of the diaper 20 is defined by the outer edges of the diaper 20 in which the longitudinal edges are oriented generally parallel to the longitudinal centerline 70 of the diaper 20 and the end edges 52 run between the longitudinal edges generally parallel to the transverse centerline 72 of the diaper 20. However, for better fit, longitudinal edges are preferably curved to produce an "hourglass" shape diaper when viewed in the flat-out configuration of FIG. 1. The chassis 22 of the diaper 20 comprises the main body of the diaper 20. The chassis 22 comprises at least the topsheet 24 and the backsheet 26.

For tape-type diapers, that is, diapers intended to be fastened about the wearer by use of an adhesive tape or releasable mechanical fastener, the diaper 20 can have a fastening system generally designated 40, as is commonly known in the art. Once fastened upon the wearer, portions of longitudinal edge define leg openings 25. For pant-type diapers, first waist region 36 is joined by suitable means to the second waist region 38, as is commonly known in the art, to make a pant-type garment having leg openings 25 defined by the non-joined portions of longitudinal edges. Joining of the waist regions can be accomplished by application of adhesive, ultrasonic bonding, compression bonding, thermal bonding, combinations thereof, and any other suitable bonding means known in the art which is appropriate for the specific materials employed.

While the topsheet 24, the backsheet 26, and the absorbent core 28 may be assembled in a variety of well-known configurations, preferred tape-diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; and U.S. Pat. No. 5,580,411 entitled "Zero Scrap Method For Manufacturing Side Panels For Absorbent Articles" which issued to Nease et al. on Dec. 3, 1996. Preferred pant-type diapers and methods for making suitable side seams are disclosed in U.S. Pat. No. 5,569,234 issued to Buell, et al. on Oct. 29, 1996, U.S. Pat. No. 5,607,537 issued to Johnson et al. on Mar. 4, 1997, U.S. Pat. No. 5,662,638 issued to Johnson et al. on Sep. 2, 1997, and U.S. Pat. No. 5,685,874 issued to Buell et al. on Nov. 11, 1997. Preferable seams are disclosed in European Patent Application No. 96118654.1 titled "Thermal Joining of Webs" filed on Nov. 21, 1996 (Christoph J. Schmitz).

The backsheet 26 is generally that portion of the diaper 20 positioned adjacent the garment facing surface of the absorbent core 28 which prevents the exudates absorbed and contained therein from soiling articles which may contact the diaper 20, such as bed sheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names XI 5306, X10962 and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and micro porous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996.

The backsheet 26 is generally that portion of the diaper 20 positioned adjacent the garment facing surface of the absorbent core 28 which prevents the exudates absorbed and contained therein from soiling articles which may contact the diaper 20, such as bed sheets and undergarments.

The backsheet 26 may be joined to the topsheet 24, the absorbent core 28 or any other element of the diaper 20 by any attachment means known in the art. For example, hot melt adhesives applied about the portions of the peripheral edges can be sufficient to join the topsheet and backsheet to one another.

The topsheet 24 is preferably positioned adjacent the body surface of the absorbent core 28 and may be joined thereto and/or to the backsheet 26 by any attachment means known in the art. The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; melt-blown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The diaper 20 can also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24. The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989.

The diaper 20 may also include a fastening system 40. In particular, tape-type diapers have a fastening system. The fastening system 40 preferably maintains the first waist region 36 and the second waist region 38 in an overlapping configuration so as to provide tension about the circumference of the waist opening of the diaper 20 to hold the diaper 20 on the wearer. The fastening system 40 preferably comprises tape tabs and/or hook and loop fastening components, although any fastening means known in the art is generally acceptable.

In pant-type diapers, opposing sides, i.e., longitudinal edge portions of first waist region 36 and second waist region 38, of the garment are seamed or welded to form a pant, as is known in the art. This allows the article to be used as a pull-on type diaper, such as a training pant.

The diaper 20 can also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may be constructed in any suitable configurations as known in the art. Examples of diapers with elasticized side panels are disclosed in U.S. Pat. No. 4,857,067, entitled Disposable Diaper Having Shirred Ears issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled Absorbent Articles Providing Sustained Dynamic Fit; U.S. patent application Ser. No. 08/155,048 entitled Absorbent Article With Multi-Directional Extensible Side Panels filed Nov. 19, 1993 in the names of Robles, et al.

The diaper 20 preferably further includes leg cuffs 32 which provide improved containment of liquids and other body exudates. Leg cuffs may also be referred to as legbands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al.

on Feb. 28, 1989 and Mar. 20, 1990, respectively, describe disposable diapers having "stand-up" elasticized flaps (barrier cuffs) that improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. Barrier leg cuff elastics 29 may be used to improve containment of urine and other body exudates.

In the prior art, diapers' longitudinal edges were left unfinished, that is, the edges of the component webs, such as the topsheet 24 and backsheet 26, were left exposed. Although functional, this configuration leaves the diaper with an unfinished look. Attempts to make the diaper more garment-like by finishing the longitudinal edges in an economical manner have thus far proved unsatisfactory. For example, the addition of separate, discrete portions of edge-finishing materials involves the cutting and accurate placement of materials on high-speed equipment which poses many difficult challenges and also increases material costs.

The method and apparatus of the present invention is directed to the making of an improved diaper having a finished edge cuff. The finished edge cuff comprises an edge fold 60 that is formed around and/or along a portion of longitudinal edge. Edge fold 60 is formed by folding and seaming existing material (e.g., backsheet, topsheet, combination backsheet and topsheet, etc.) and does not require the addition of a discrete part. Edge fold 60 can be extensible, and can be elastic or highly elastic, or rendered elastic or highly elastic. Preferably, each edge fold 60 has dimensions such that when the diaper 20 is worn, the edge fold 60 completely encircles the portion of longitudinal edge that defines the leg opening 25. The method and apparatus may also include the additional steps/operations of activation, slitting and/or cutting. A variety of diaper designs and their corresponding methods of manufacture will now be discussed.

Referring first to FIGS. 2-8, non-limiting exemplary embodiments of diapers having finished edge folds 60 are shown. For illustrative purposes, the method of manufacturing these exemplary diapers will be discussed in an exemplary order of the steps being used. Additionally, some of the differences between each diaper within each step will also be discussed. For clarity, in FIGS. 2-8, layer(s) of material superjacent to the elastic 31 are illustrated as transparent.

Activation

One step in preparing the chassis 22 for the subsequent creation of an edge fold 60 is "activation" (also referred to as incremental stretching) of at least a portion of longitudinal edge. Incremental stretching methods and suitable incrementally stretched materials are described in commonly assigned U.S. Pat. No. 5,167,897 issued to Weber et al. on Dec. 1, 1992; U.S. patent application Ser. No. 09/897,823 and U.S. patent application Ser. No. 10/179,696. An activated or incrementally stretched laminate (e.g., laminate having an elastomeric material layered between two elastomeric materials) is formed with the non-elastomeric material in a substantially relaxed, i.e., non-stretched state. The laminate is then incrementally stretched, resulting in the non-elastomeric material being strained beyond its elastic limit and in the creation of plastically deformed areas of the non-elastomeric material, which areas generally remain laminated with the elastomeric material. In some embodiments, the laminate can be incrementally stretched to the elastic limit of the elastomeric material. In the finished incrementally stretched laminate in a relaxed state, the cumulative bulk of the non-elastomeric material may be substantially no more than that of the original laminate prior to its being incrementally stretched. Thus, both the maximum elastic extension and the elastic extensibility of an incrementally stretched laminate may be significantly greater than those of a conventionally gathered structure. Activation may be used to create stretch properties in the material. Activation may also be used to create high and low density portions in the material, whereupon the contraction of incorporated elastics forms substantially uniform gathers ("uniform" defined herein as having a specific, repeatable or consistent appearance). In most instances, the pitch of the gathers is determined by the distance between the tips of the teeth on the activation tooling (see FIGS. 9-11). Various and varied pitch dimensions may be used so long as the gathers appear to be substantially uniform.

Figure 6B:
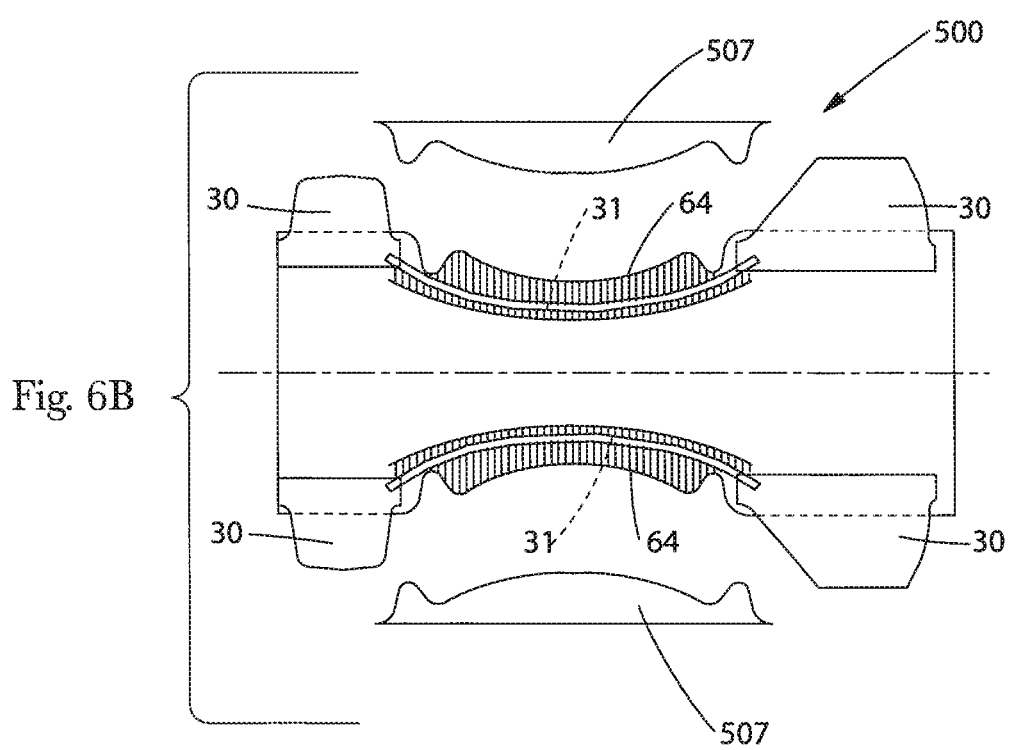
FIG. 6B is a bottom view of the fifth embodiment in FIG. 6 after being processed by the manufacturing step of cutting.
Figure 5:
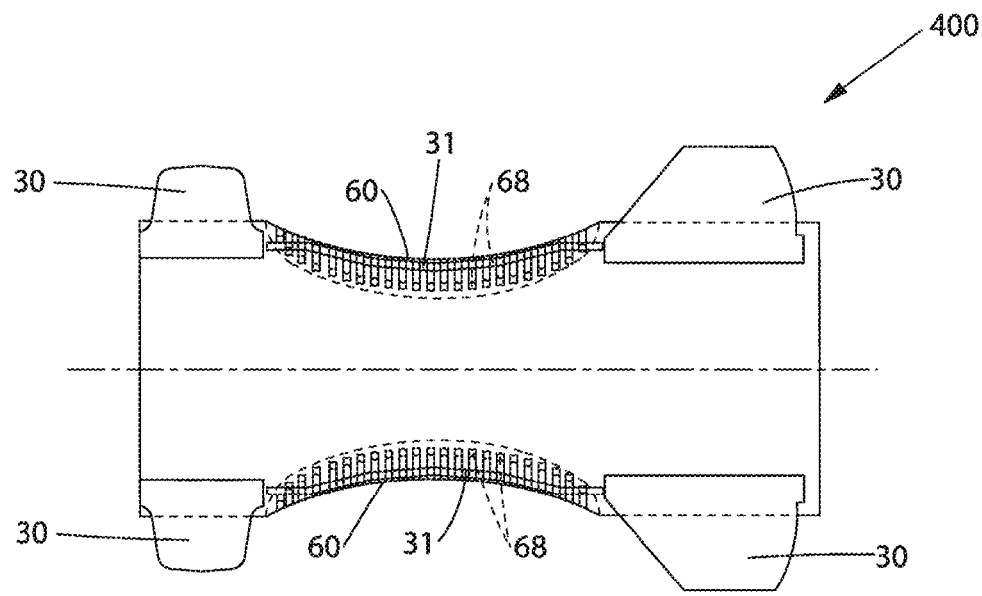
FIG. 5 is a bottom view of a fourth embodiment of an absorbent article of the present invention.
Figure 6:
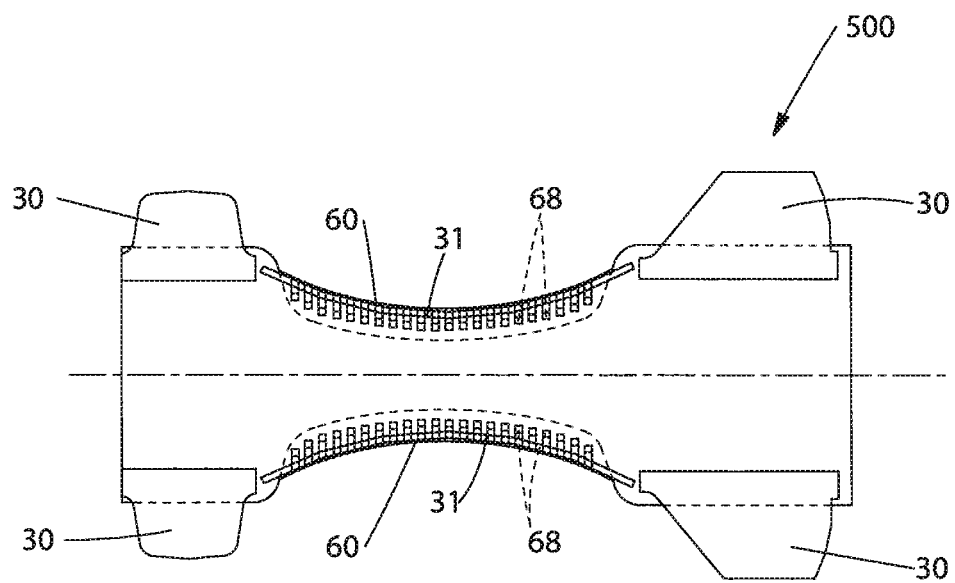
FIG. 6 is a bottom view of a fifth embodiment of an absorbent article of the present invention.
Figure 5A:
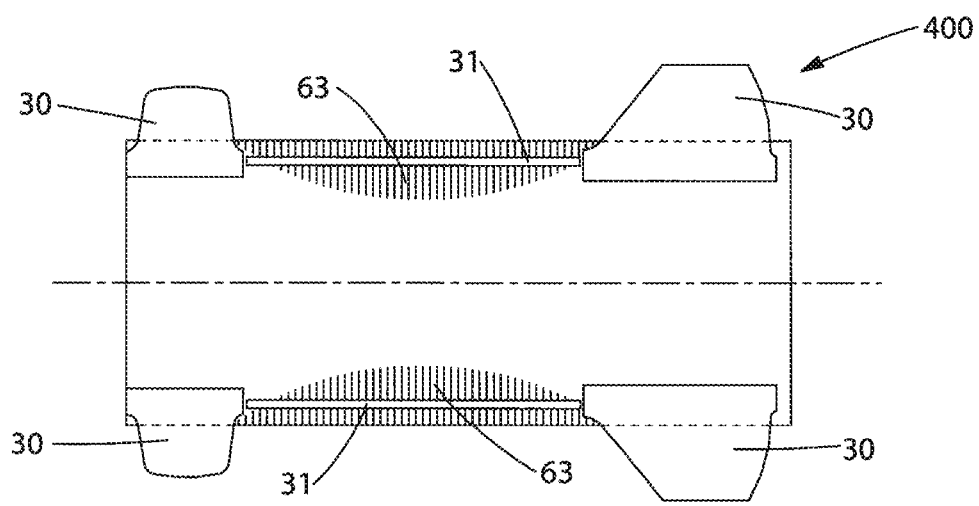
FIG. 5A is a bottom view of the fourth embodiment in FIG. 5 after being processed by the manufacturing step of activation.
Figure 6A:
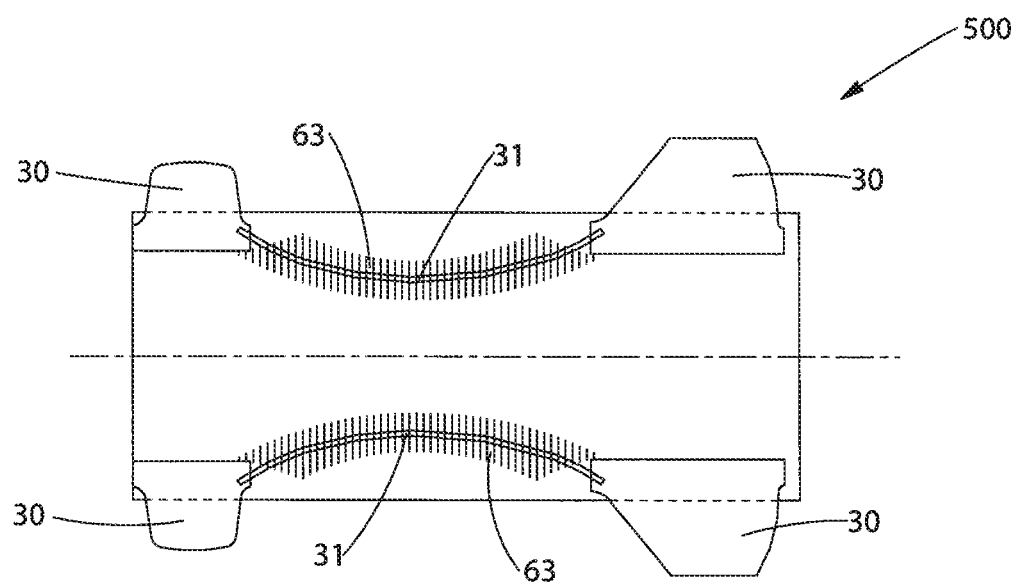
FIG. 6A is a bottom view of the fifth embodiment in FIG. 6 after being processed by the manufacturing step of activation.

Referring now to FIGS. 2A-6A (diapers 100, 200, 300, 400, 500, respectively), a "multi-piece" chassis 22 (herein defined as a chassis having attached side panels 30; in contrast to a "uni-body" chassis having integral side panels and having a final shape determined by a side notch cut) is shown having at least a portion of longitudinal edge activated to strain and/or break fibers, said portion being identified as activated portion 63. In these exemplary embodiments, substantially the entire portion of the longitudinal edge between the side panels 30 is activated. In this way, an edge fold 60 may substantially cover the entire circumference of the completed leg opening 25. However, a smaller portion of longitudinal edge may also be activated and still be appreciated within the present invention. In FIGS. 2A-4A, activated portion 63 is substantially linear. FIG. 5A shows activated portion 63 being substantially arched and beginning from the longitudinal edge. FIG. 6A shows activated portion 63 being arched and not beginning from the longitudinal edge. These non-limiting examples of activated portions 63 provide for a variety of different types of folding techniques which may ultimately lead to a variety of different shaped edge folds 60 (discussed infra).

Referring to FIGS. 7A-8A (diapers 600, 700, respectively), activated portions 63 are created on a non-formed chassis (herein defined as a chassis not yet having attached or defined side panels 30, e.g., material web not yet cut or shaped). Activated portions 63 may be formed inboard to longitudinal edge in an area which will later serve to be the leg opening 25. Activated portions 63 may preferably be created in the machine direction, wherein, the elongation of said activated portions allows additional stretch in the machine direction.

Figure 9:
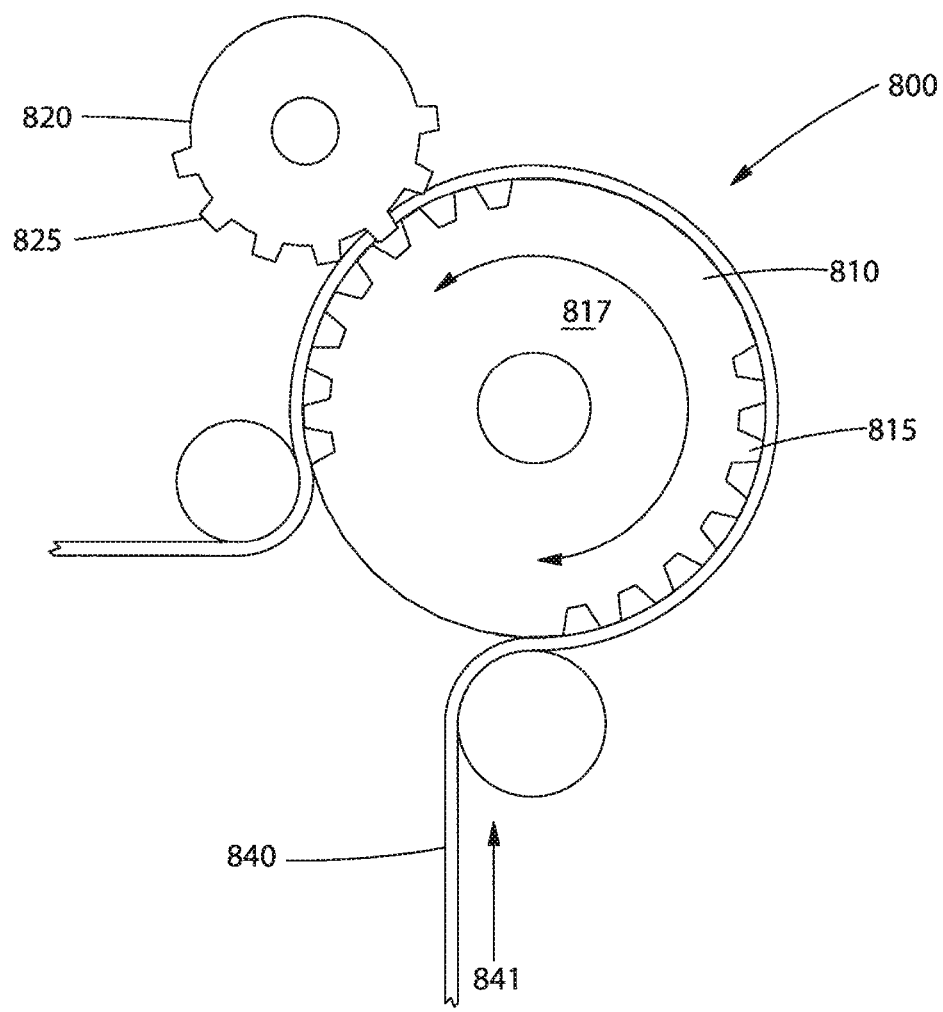
FIG. 9 shows a first exemplary embodiment of an activation apparatus that is capable of performing the manufacturing step of activation.

FIG. 9 shows a first exemplary embodiment of activation apparatus 800 that is capable of performing said activation process. A first roll 810 having teeth 815 and a second roll 820 having teeth 825 engage to mate with one another. In this particular example, first roll 810 supplies heat (e.g., conductive heat, radiant heat, convective heat, hot gas, hot air, etc.) through the lower base portion of teeth 815 within the radial region 817. When a material 840 is fed in a direction indicated by arrow 841 through said apparatus 800, material 840 is first exposed to said heat and then to mating teeth 815, 825 to thus activate said material.

Figure 10:
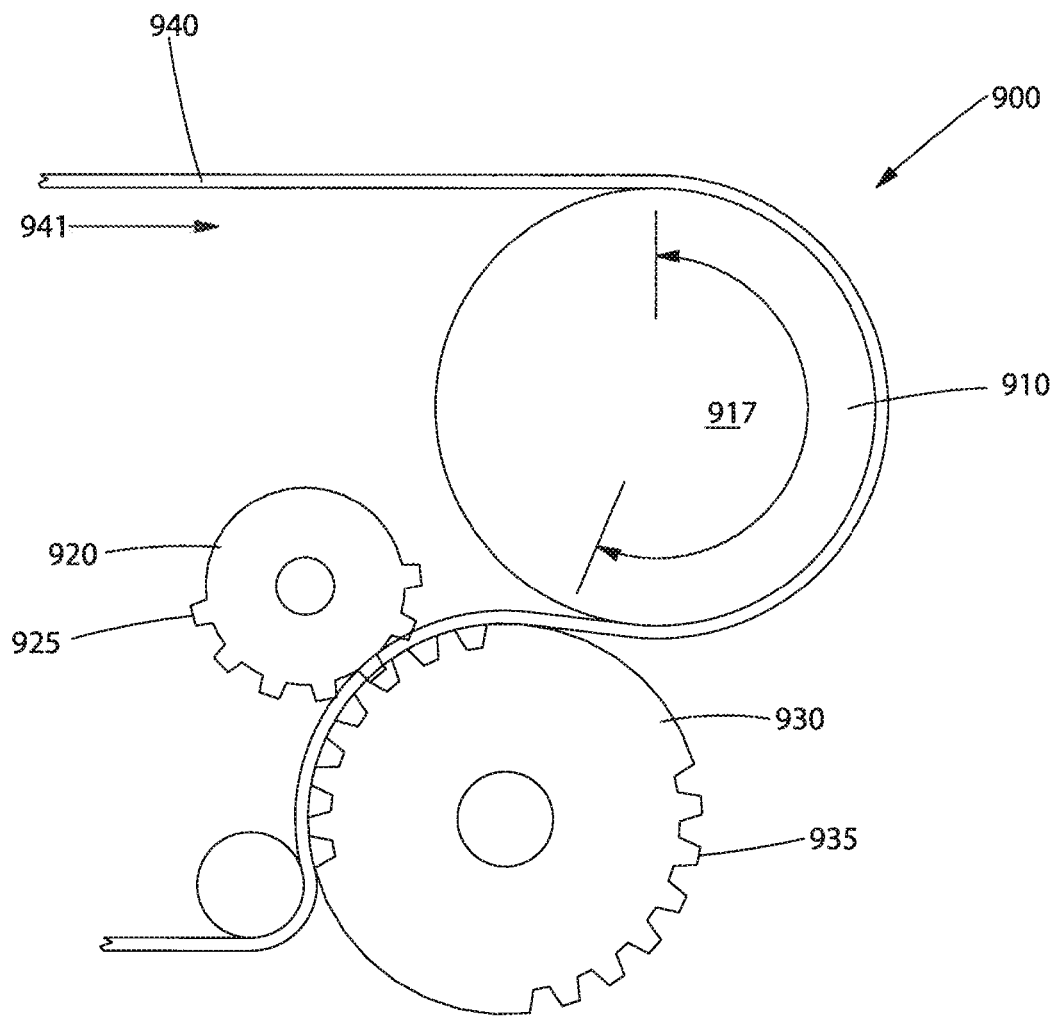
FIG. 10 shows a second exemplary embodiment of an activation apparatus that is capable of performing the manufacturing step of activation.

FIG. 10 shows a second exemplary embodiment of activation apparatus 900 that is capable of performing said activation process. A first roll 910 is capable of supplying heat in radial region 917. A second roll 920 having teeth 925 and a third roll 930 having teeth 935 engage to mate with one another. When a material 940 is fed in a direction indicated by arrow 941 through said apparatus 900, material 940 is first exposed to heat via first roll 910 and then to mating teeth 925, 935 to thus activate said material.

Figure 11:
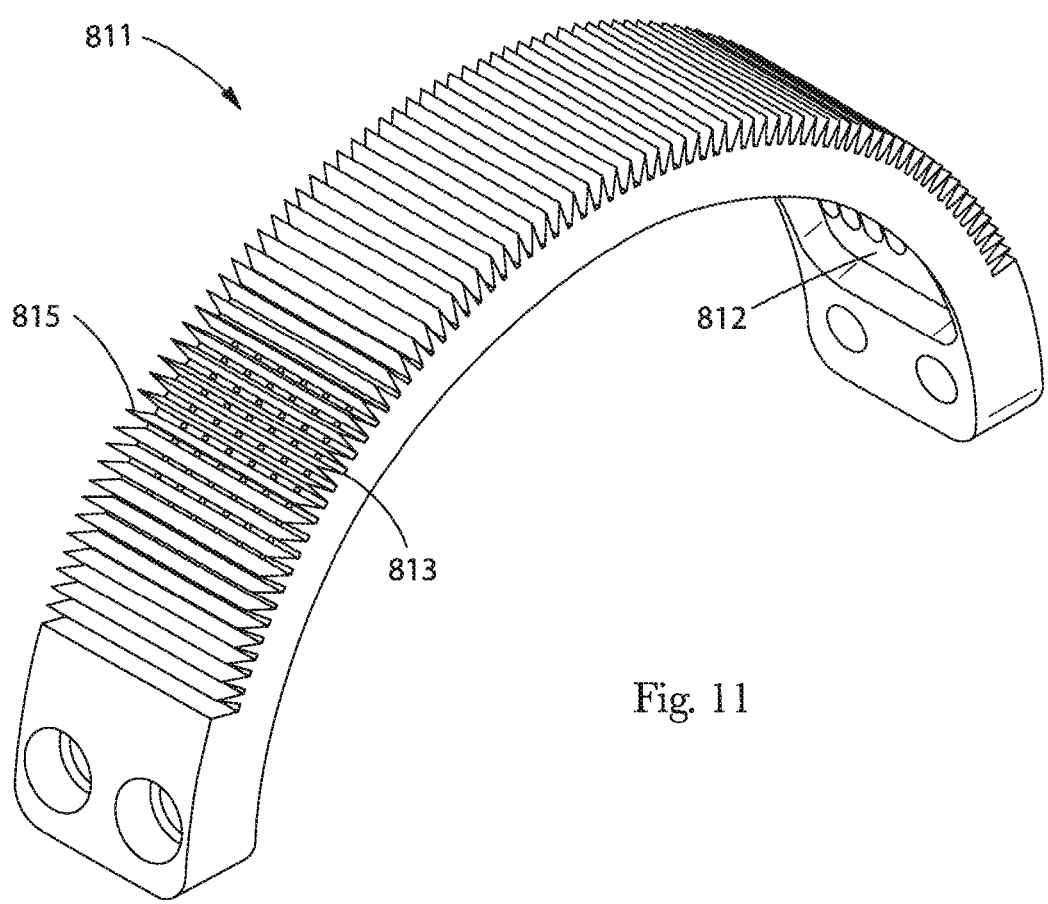
FIG. 11 shows an exemplary embodiment of a segment of a first roll having teeth that may be used in the apparatus of FIGS. 9 and 10.

FIG. 11 shows an exemplary embodiment of a segment 811 of first roll 810 having teeth 815. Heat is supplied through the underneath side of segment 811 through a distribution chamber 812 and then through holes 813 positioned in between teeth 815.

Additional details and teachings of activation may be found in commonly assigned U.S. Pat. Nos. 6,500,377; 5,167,897; 5,156,793; 5,143,679; 5,527,304; 5,674,216; 5,628,741; 5,914,084; 6,114,263; 5,779,691; 5,591,155, which are hereby incorporated by reference.

Cutting

Figure 7:
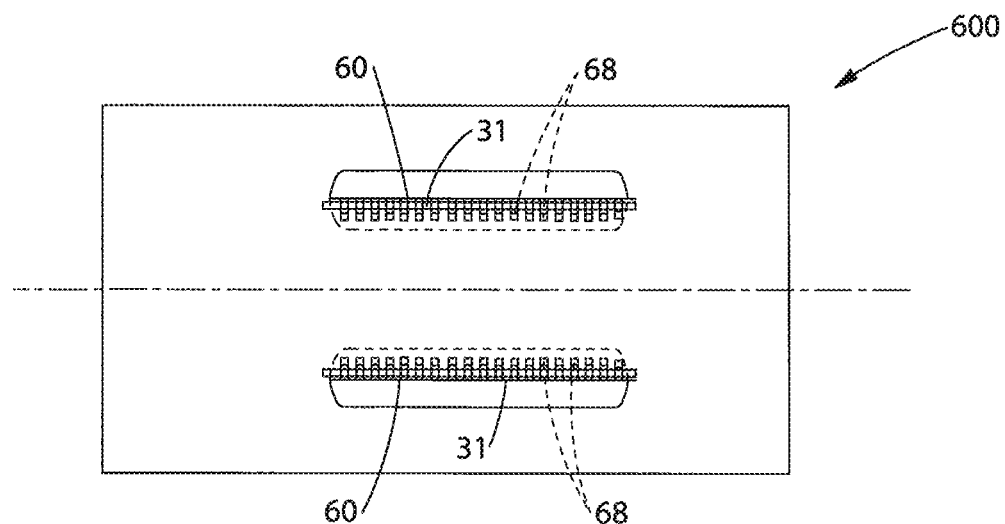
FIG. 7 is a bottom view of a sixth embodiment of an absorbent article of the present invention.
Figure 7A:
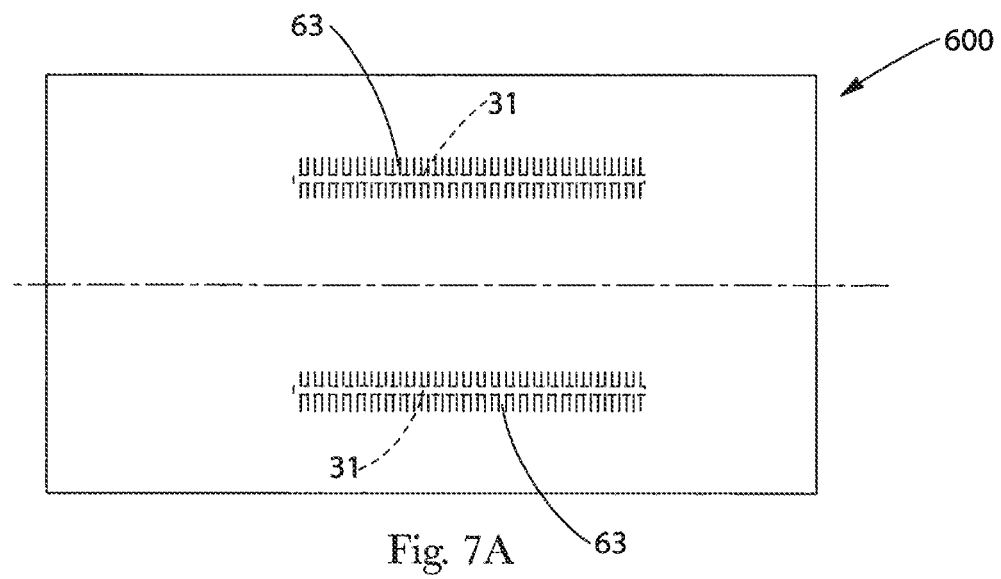
FIG. 7A is a bottom view of the sixth embodiment in FIG. 7 after being processed by the manufacturing step of activation.
Figure 7B:
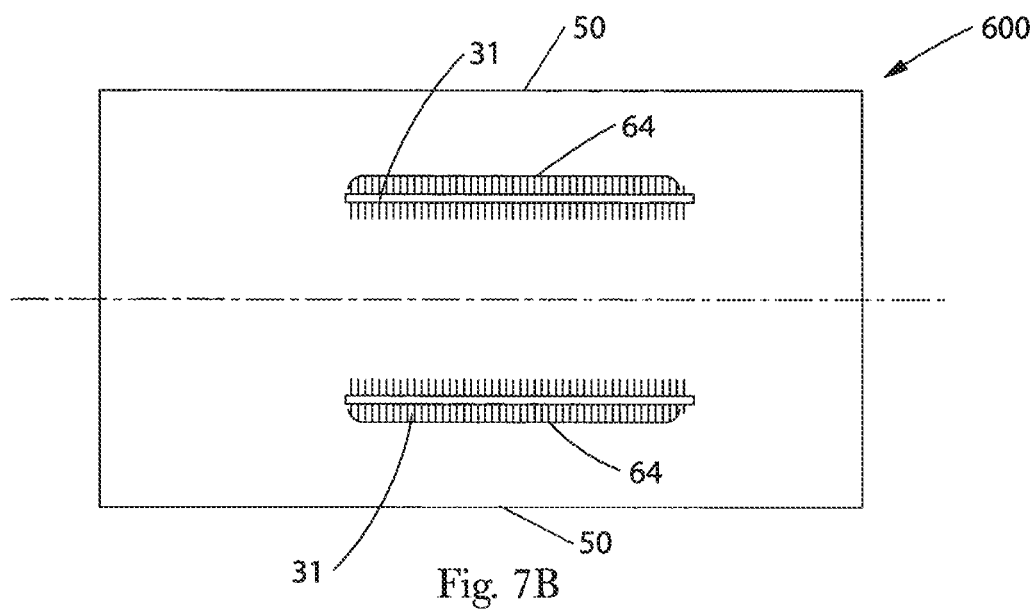
FIG. 7B is a bottom view of the sixth embodiment in FIG. 7 after being processed by the manufacturing step of cutting.
Figure 8B:
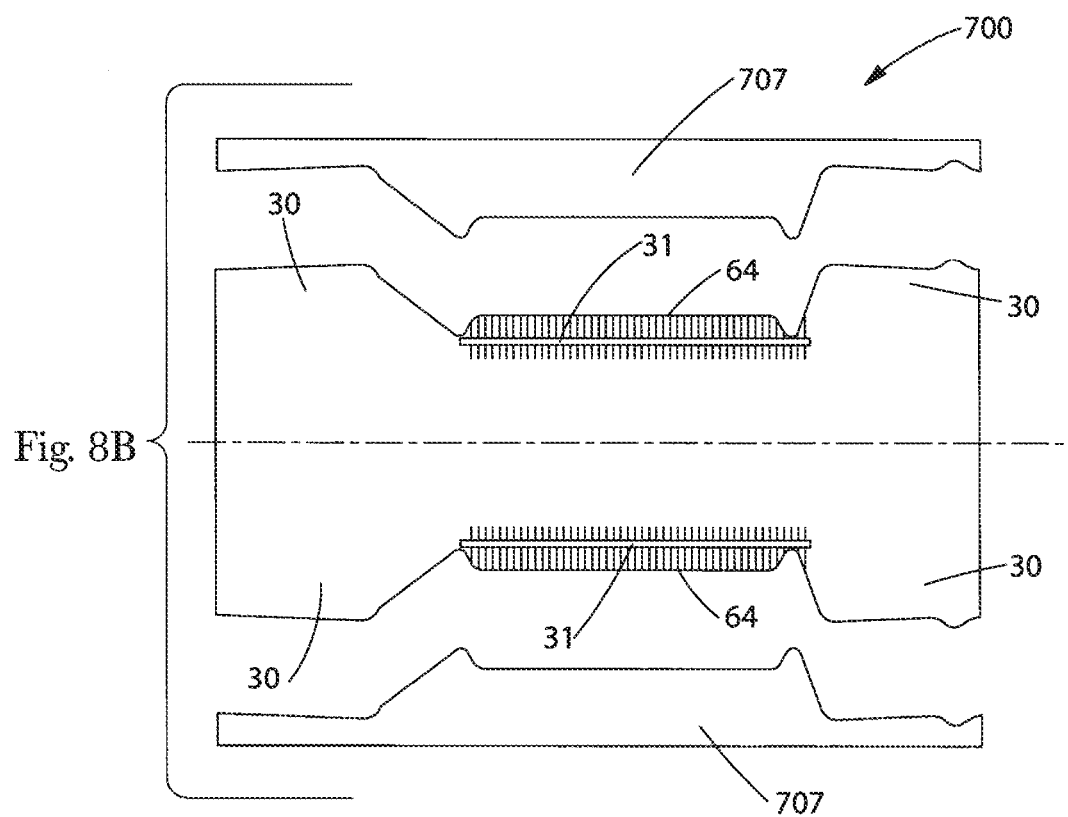
FIG. 8B is a bottom view of the seventh embodiment in FIG. 8 after being processed by the manufacturing step of cutting.

In another step of forming edge fold 60, the activated chassis may be cut. Said cutting step may be incorporated to assist in the subsequent folding step in that the cut helps the longitudinal edge fold onto the chassis. For example, in FIG. 4B, a simple cut 64 of minimal length is made substantially perpendicular to longitudinal edge. In another example, FIG. 7b, a simple cut 64 of moderate length is made substantially parallel to longitudinal edge. In yet another example, in FIGS. 6B and 8B, a more complex cut 64 is made which provides the shaping for leg opening 25. Additionally, trim 507 and trim 707 (i.e., waste material) are removed. While cut 64 may be helpful, it is not required for subsequent folding, as exampled by the lack of corresponding "B" figures for FIGS. 2, 3 and 5 (i.e., FIGS. 2B, 3B and 5B do not exist).

Folding

In yet another step of forming edge fold 60, the activated chassis is folded. For clarity, in FIGS. 2C-8C, layer(s) of material superjacent to the elastic 31 are illustrated as transparent. Referring now to FIG. 2C, a fold 66 is made over the entire length of longitudinal edge. Said fold 66 may be made using a folding board or other known techniques. In this way, the side panels 30 are also folded over. Fold 66 may be formed such that the leg elastic 31 (also known as an outer cuff elastic) is now positioned in close proximity to the newly-formed edge fold 60. After this fold step, the original longitudinal edge is moved inboard and is now identified as leading fold end 53. While only one leg elastic 31 is shown on each side of chassis 22, one skilled in the art would appreciate that additional leg elastics 31 may also be contemplated. When said leg elastics 31 are applied to chassis 22, a multitude of affixing techniques may be utilized including, but not limited to, applying adhesive to substantially the entire length of leg elastic 31, applying adhesive to the ends of leg elastic 31 (i.e., drawstring method; e.g., for curved elastics in FIGS. 5 and 6), etc.

Figure 2:
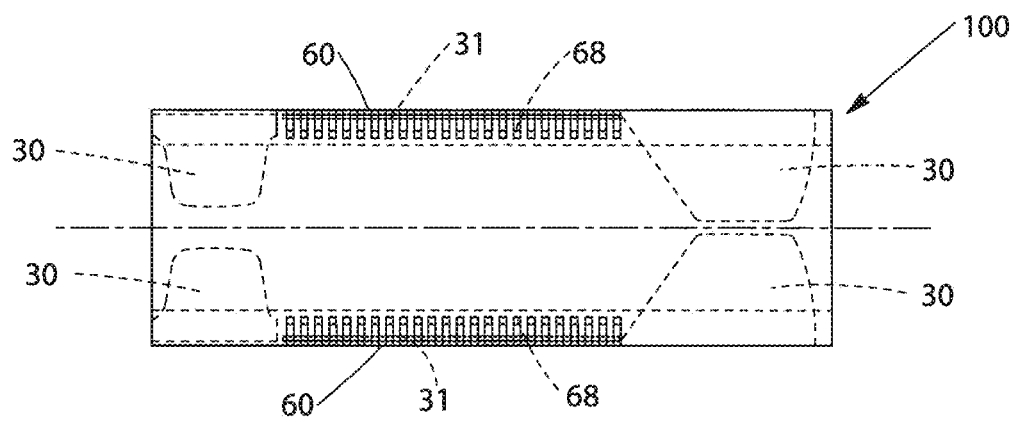
FIG. 2 is a bottom view of a first embodiment of an absorbent article of the present invention.
Figure 3:
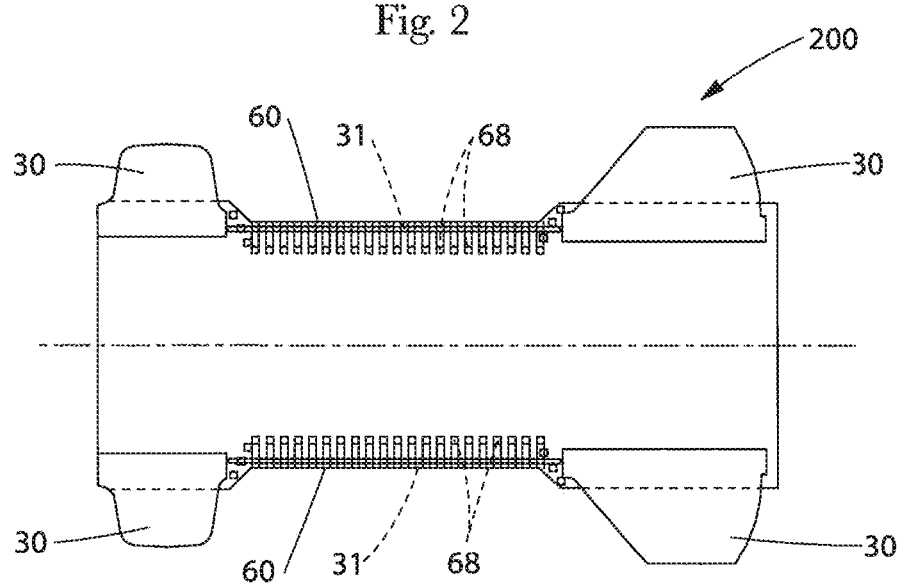
FIG. 3 is a bottom view of a second embodiment of an absorbent article of the present invention.
Figure 4:
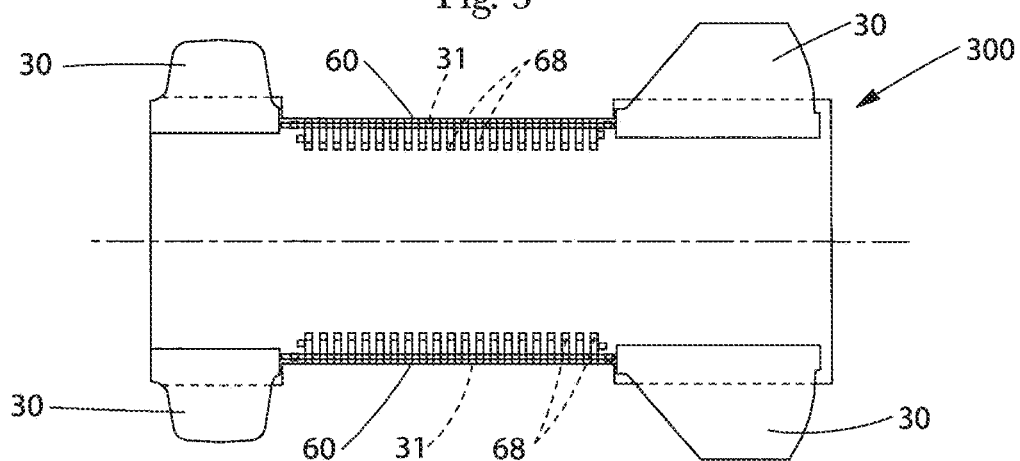
FIG. 4 is a bottom view of a third embodiment of an absorbent article of the present invention.
Figure 2A:
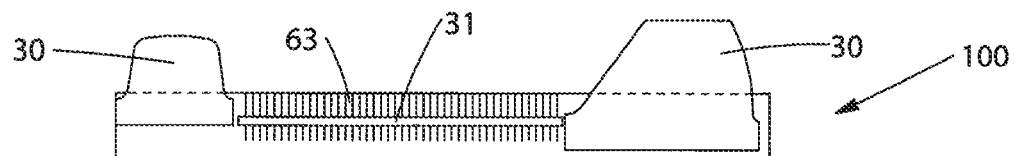
FIG. 2A is a bottom view of the first embodiment in FIG. 2 after being processed by the manufacturing step of activation.
Figure 3A:
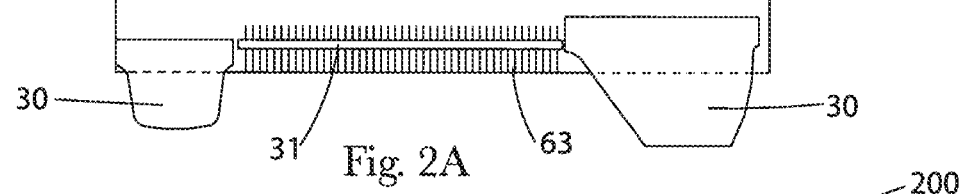
FIG. 3A is a bottom view of the second embodiment in FIG. 3 after being processed by the manufacturing step of activation.
Figure 4A:
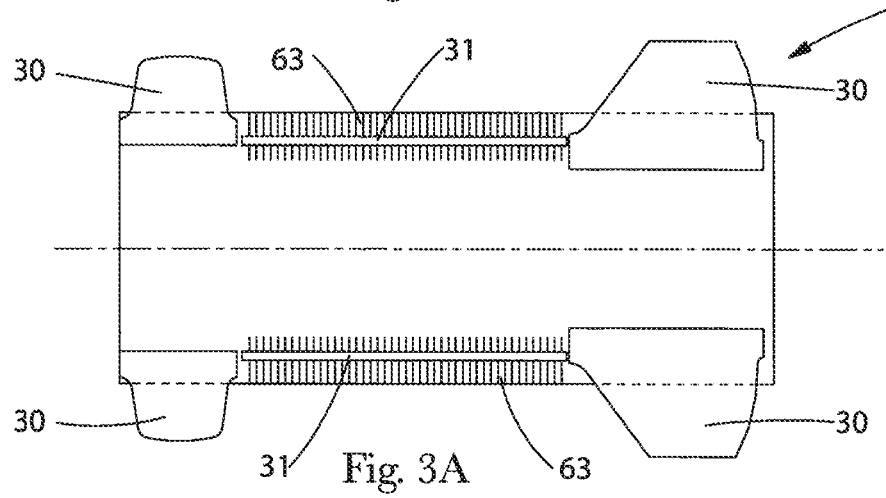
FIG. 4A is a bottom view of the third embodiment in FIG. 4 after being processed by the manufacturing step of activation.
Figure 4B:
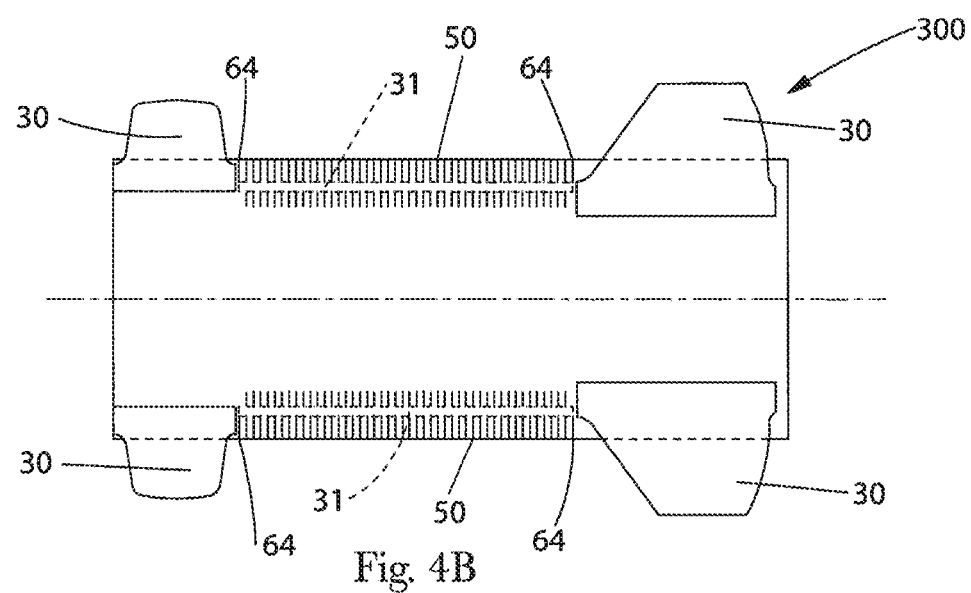
FIG. 4B is a bottom view of the third embodiment in FIG. 4 after being processed by the manufacturing step of cutting.
Figure 2C:
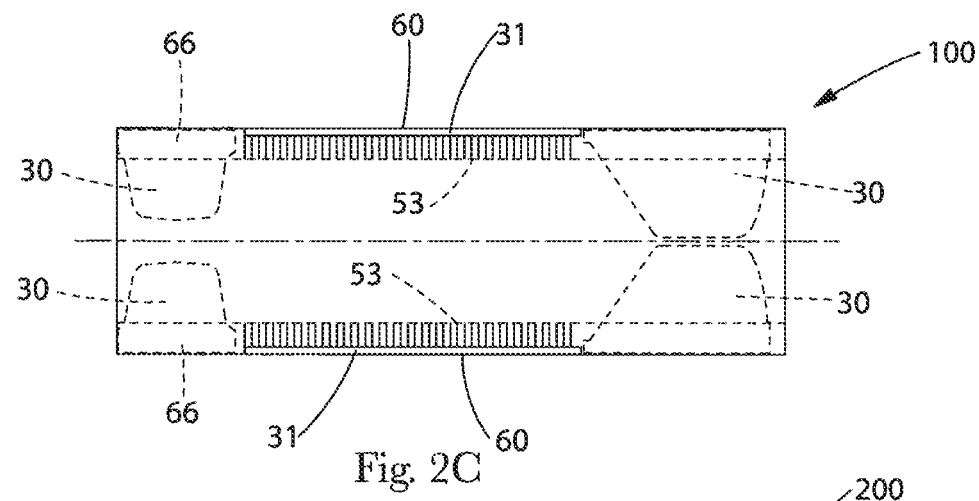
FIG. 2C is a bottom view of the first embodiment in FIG. 2 after being processed by the manufacturing step of folding.
Figure 3C:
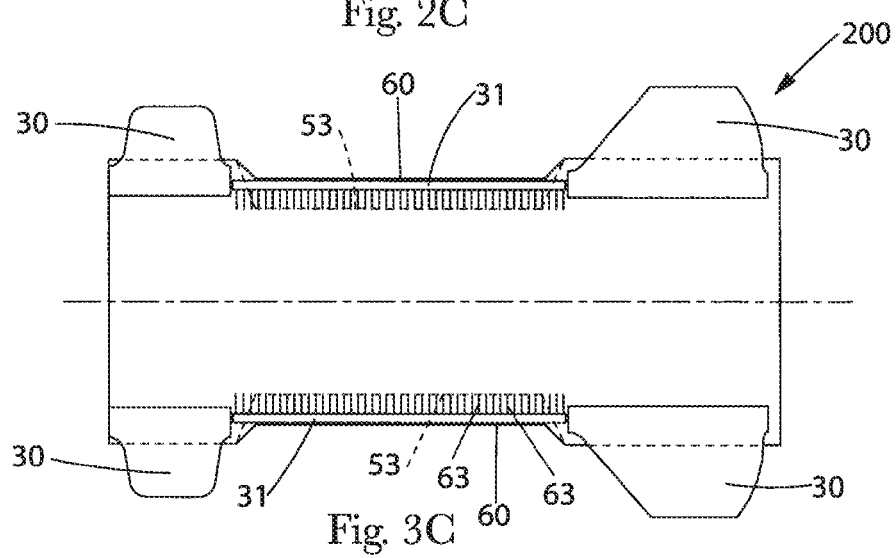
FIG. 3C is a bottom view of the second embodiment in FIG. 3 after being processed by the manufacturing step of folding.
Figure 4C:
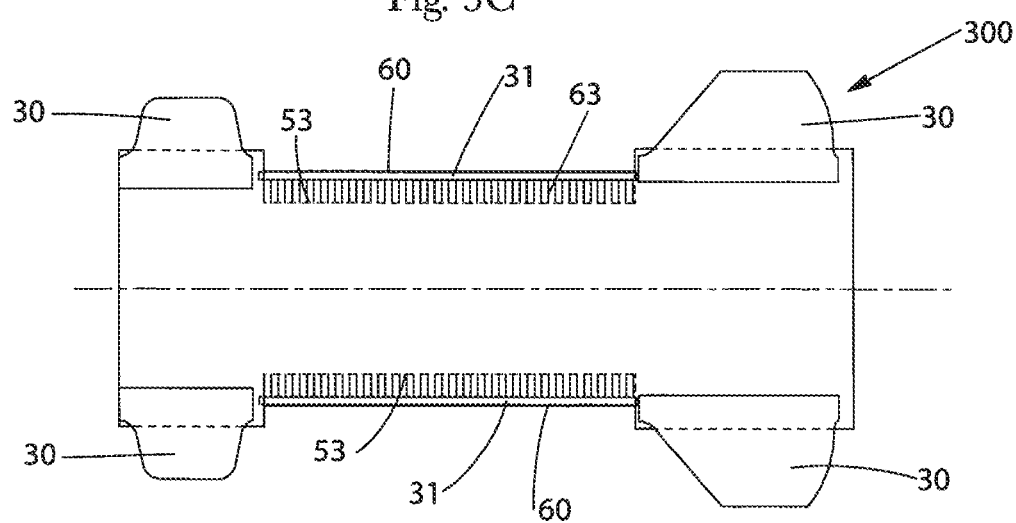
FIG. 4C is a bottom view of the third embodiment in FIG. 4 after being processed by the manufacturing step of folding.
Figure 2D:
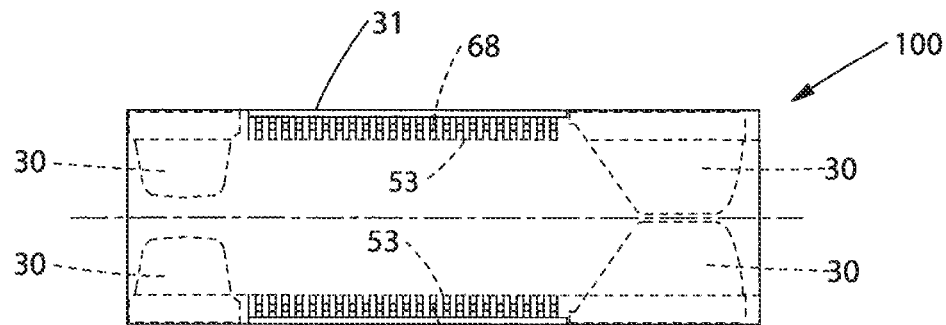
FIG. 2D is a bottom view of the first embodiment in FIG. 2 after being processed by the manufacturing step of bonding.
Figure 3D:
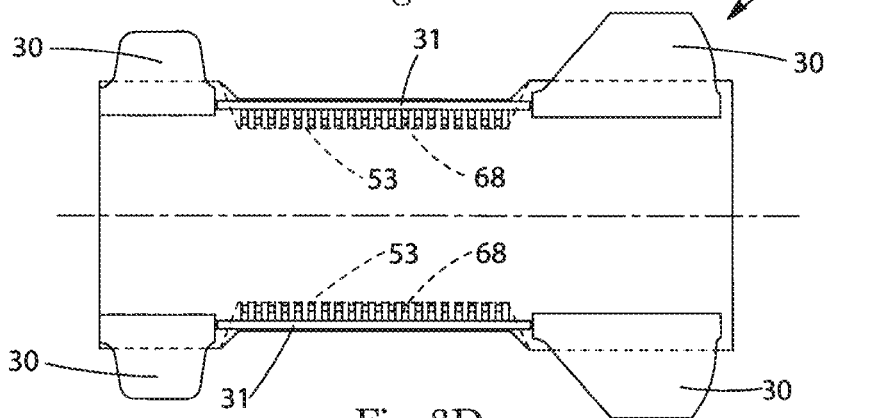
FIG. 3D is a bottom view of the second embodiment in FIG. 3 after being processed by the manufacturing step of bonding.
Figure 4D:
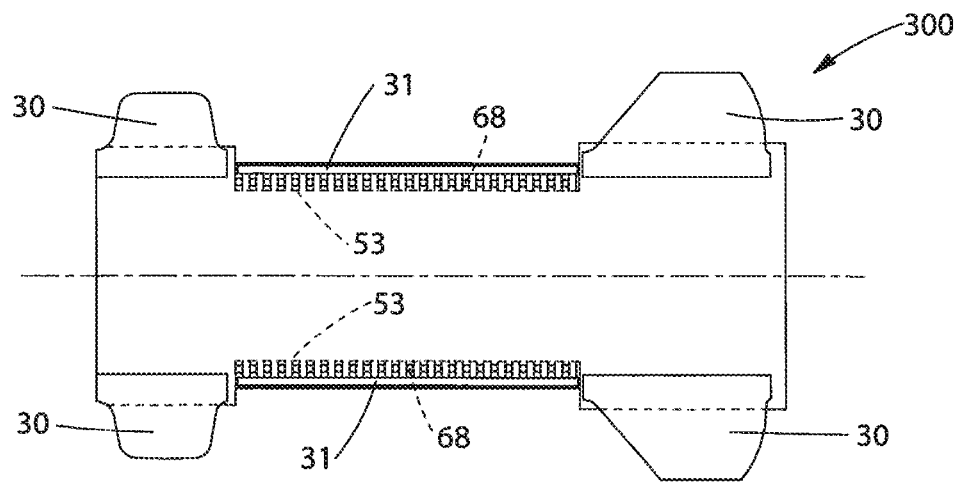
FIG. 4D is a bottom view of the third embodiment in FIG. 4 after being processed by the manufacturing step of bonding.

Referring now to FIGS. 3C and 4C, a fold 66 is made on a portion of longitudinal edge between side panels 30 by a folding rotary drum, for example, discussed infra, rather than by a folding board as in FIG. 2. In this way, the side panels are not folded over. In comparing FIG. 3C to FIG. 4C, it should be noted that because of cut 64 (see FIG. 4B) the fold in FIG. 4C is more tailored (i.e., contoured) than that of FIG. 3C (which was not previously cut), as depicted by the activated portion 63 which extends beyond the leading fold end 53 in FIG. 3C.

Figure 5C:
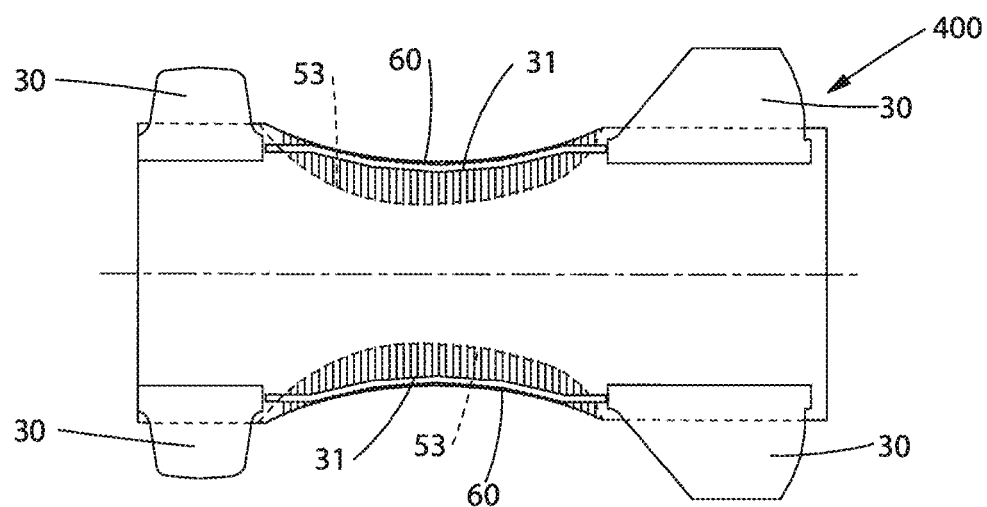
FIG. 5C is a bottom view of the fourth embodiment in FIG. 5 after being processed by the manufacturing step of folding.
Figure 6C:
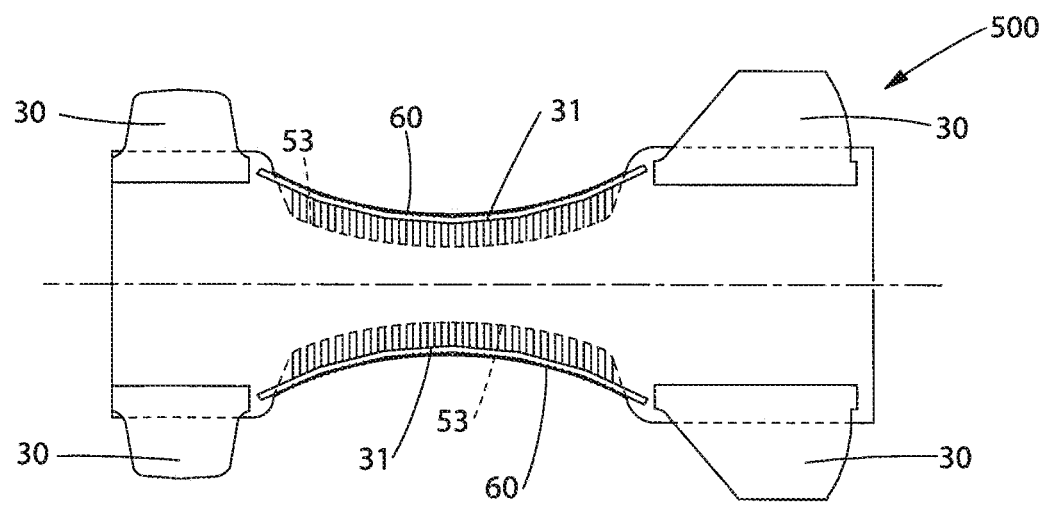
FIG. 6C is a bottom view of the fifth embodiment in FIG. 6 after being processed by the manufacturing step of folding.
Figure 5D:
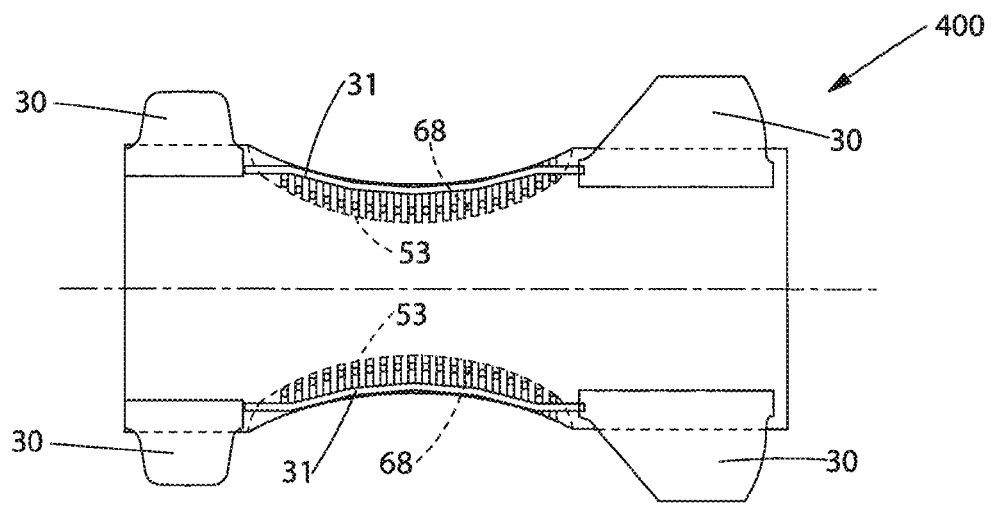
FIG. 5D is a bottom view of the fourth embodiment in FIG. 5 after being processed by the manufacturing step of bonding.
Figure 6D:
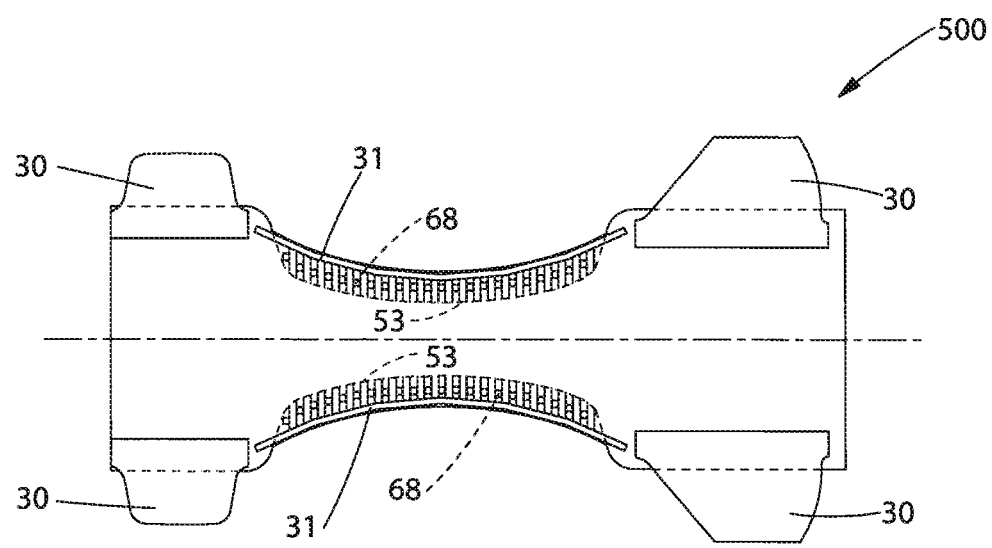
FIG. 6D is a bottom view of the fifth embodiment in FIG. 6 after being processed by the manufacturing step of bonding.
Figure 8:
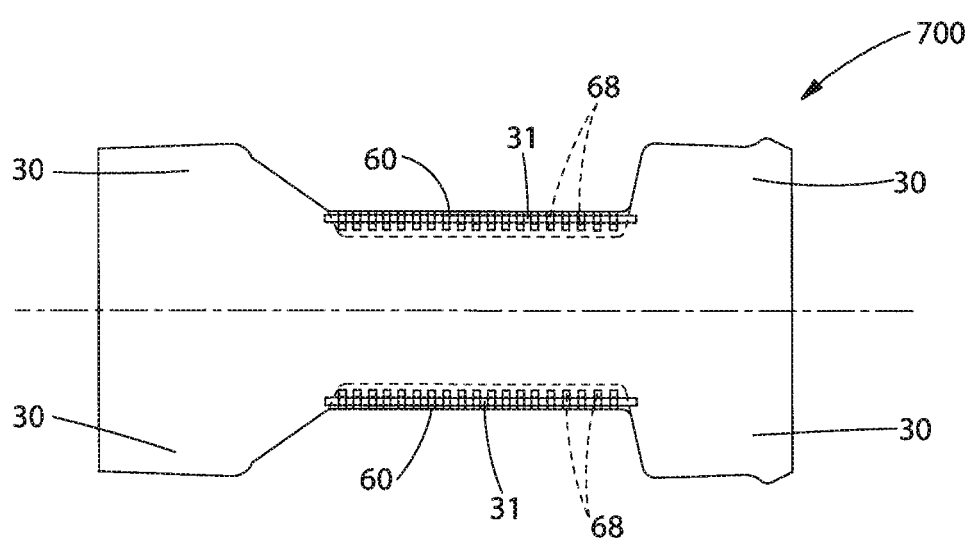
FIG. 8 is a bottom view of a seventh embodiment of an absorbent article of the present invention.
Figure 8A:
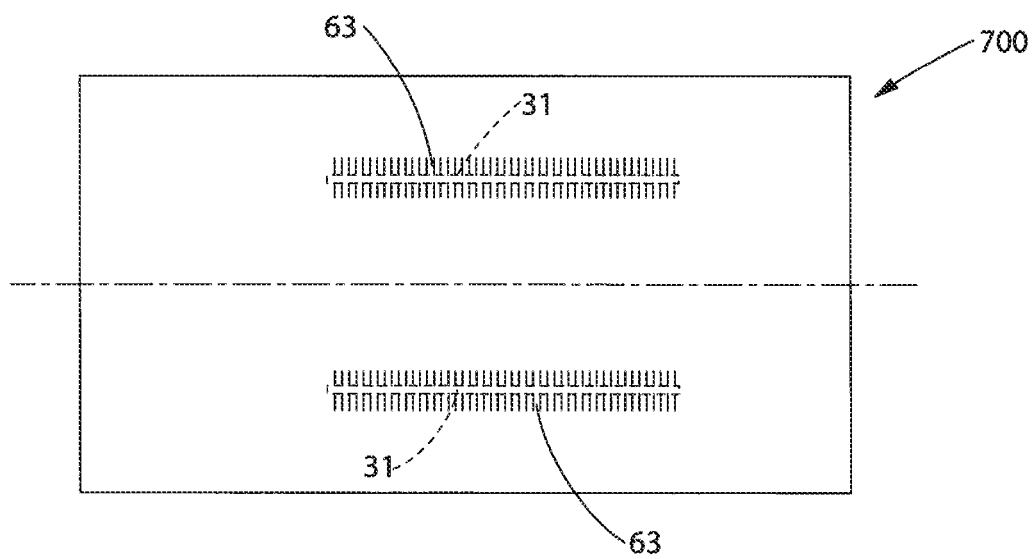
FIG. 8A is a bottom view of the seventh embodiment in FIG. 8 after being processed by the manufacturing step of activation.

Referring now to FIGS. 5C and 6C, a fold 66 is made on a portion of longitudinal edge between side panels 30 such that said fold 66 is substantially curved in shape to provide improved fit and leak-prevention benefits. In comparing FIG. 5C to FIG. 6C, it should be noted that because of cut 64 (see FIG. 6B) the fold in FIG. 6c is more tailored (i.e., contoured) than that of FIG. 5C (which was not previously cut), as depicted by the positioning of leg elastic 31 substantially along edge fold 60 in FIG. 6C. While FIG. 6C provides a more tailored fold, FIG. 5C provides the unique advantage of providing a shaped diaper 20 that has a corresponding manufacturing process that does not require cutting or trim removal.

Figure 7C:
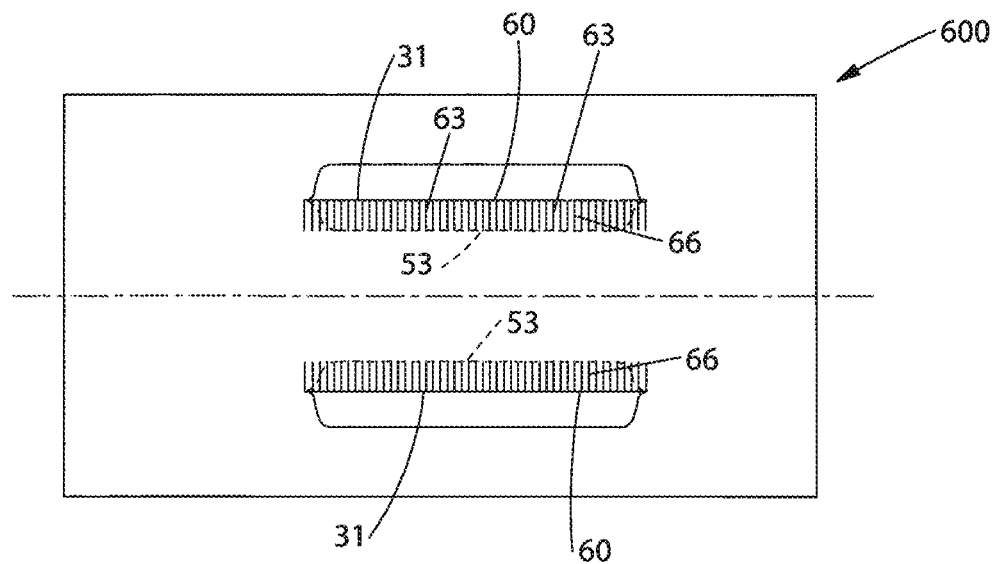
FIG. 7C is a bottom view of the sixth embodiment in FIG. 7 after being processed by the manufacturing step of folding.
Figure 8C:
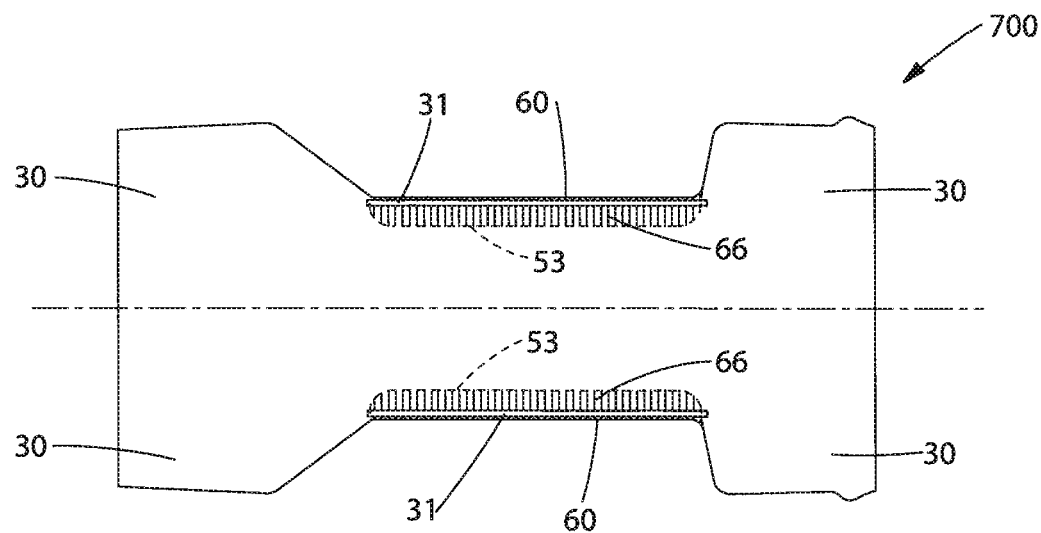
FIG. 8C is a bottom view of the seventh embodiment in FIG. 8 after being processed by the manufacturing step of folding.
Figure 7D:
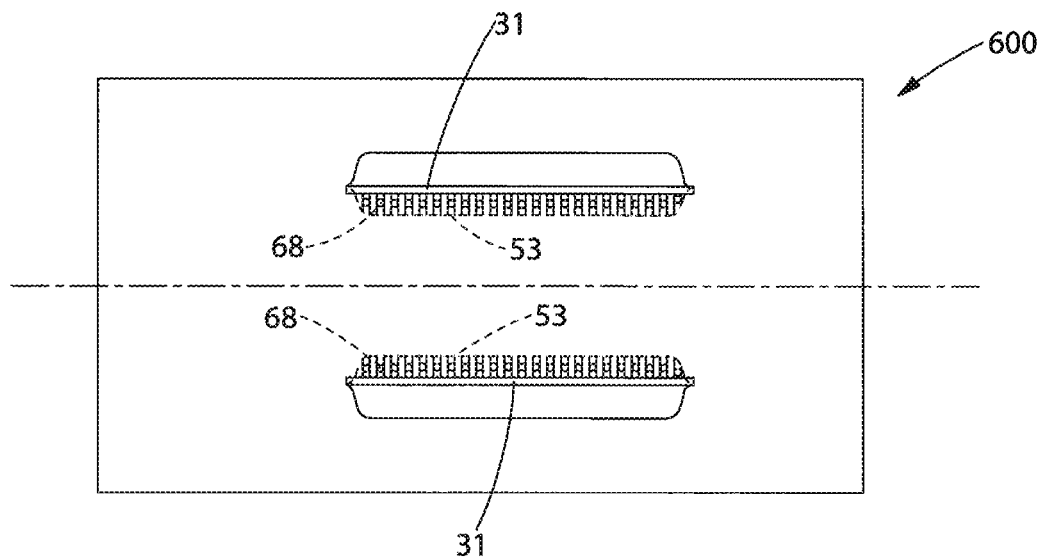
FIG. 7D is a bottom view of the sixth embodiment in FIG. 7 after being processed by the manufacturing step of bonding.
Figure 8D:
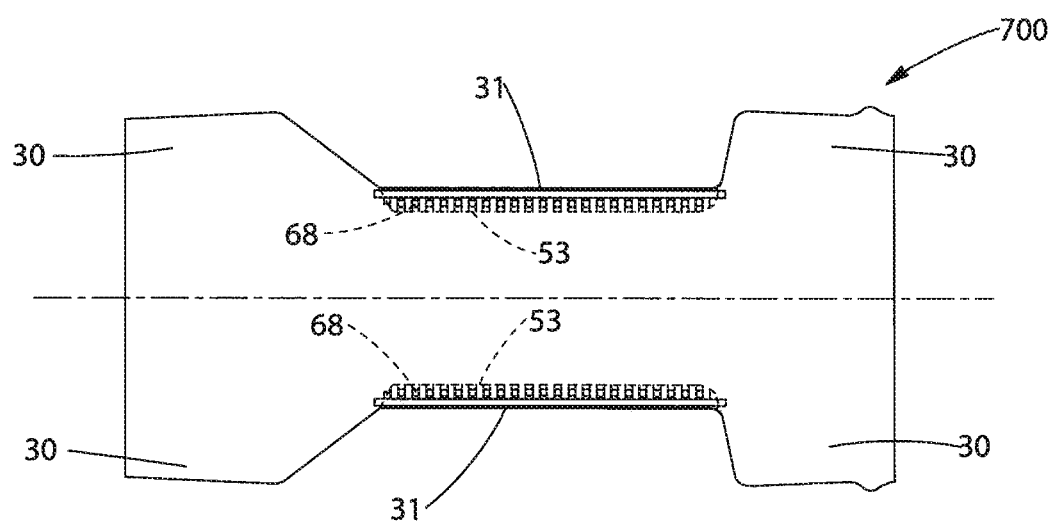
FIG. 8D is a bottom view of the seventh embodiment in FIG. 8 after being processed by the manufacturing step of bonding.

Referring now to FIG. 7C, a fold 66 is made inboard of longitudinal edge, more specifically, fold 66 is made in close proximity and substantially parallel to leg elastic 31. Because FIG. 7C was not trimmed to create leg openings 25, a final cutting/shaping will performed later. Referring now to FIG. 8C, a fold 66 is made on a portion of a new longitudinal edge between side panels 30. The notched-cut of FIG. 8B, allows the folding in FIG. 8C to be more tailored (i.e., contoured) than that of FIG. 7, as depicted by the activated portion 63 which extends beyond the leading fold end 53 in FIG. 7C.

Figure 12A:
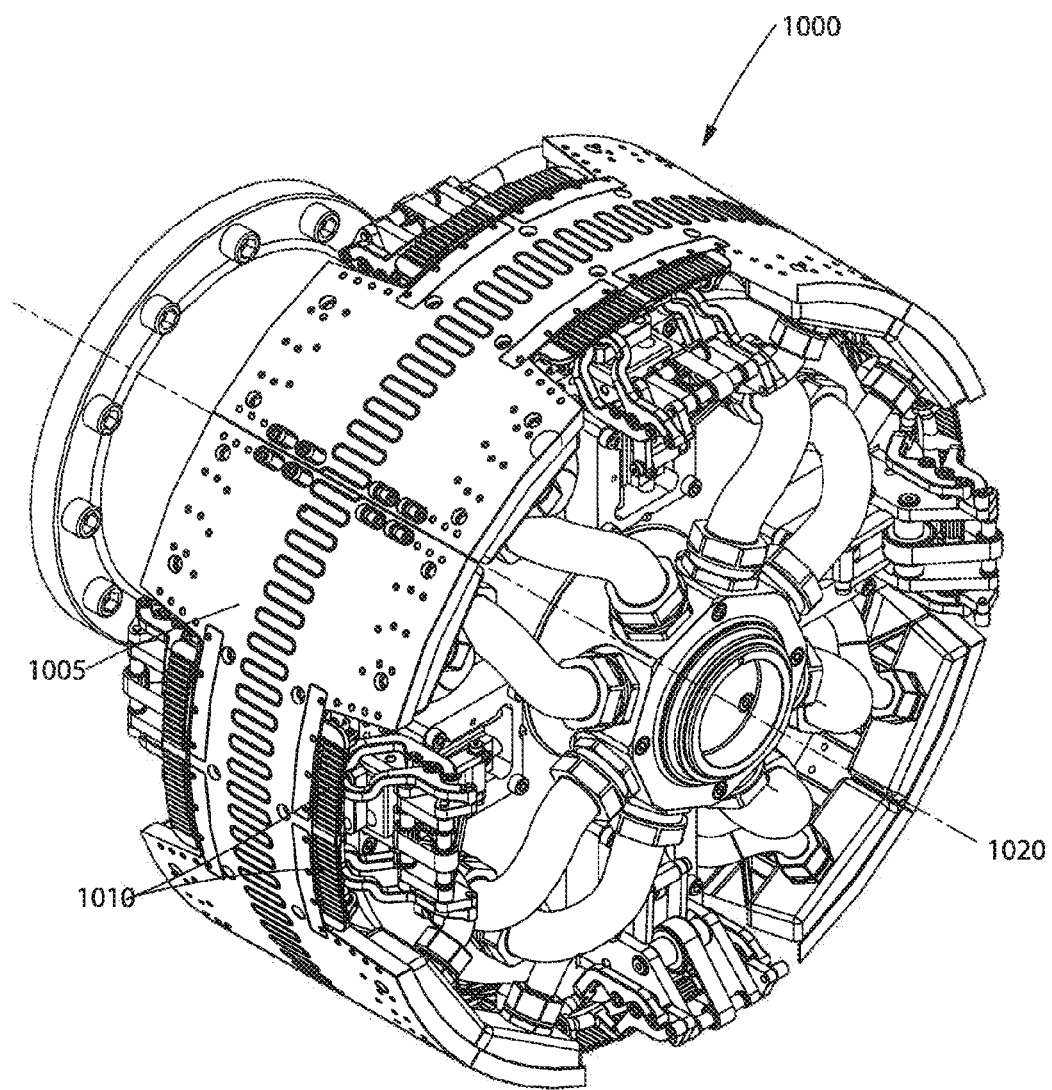
FIG. 12A shows an exemplary embodiment of a folding apparatus that is capable of performing said folding process.
Figure 12B:
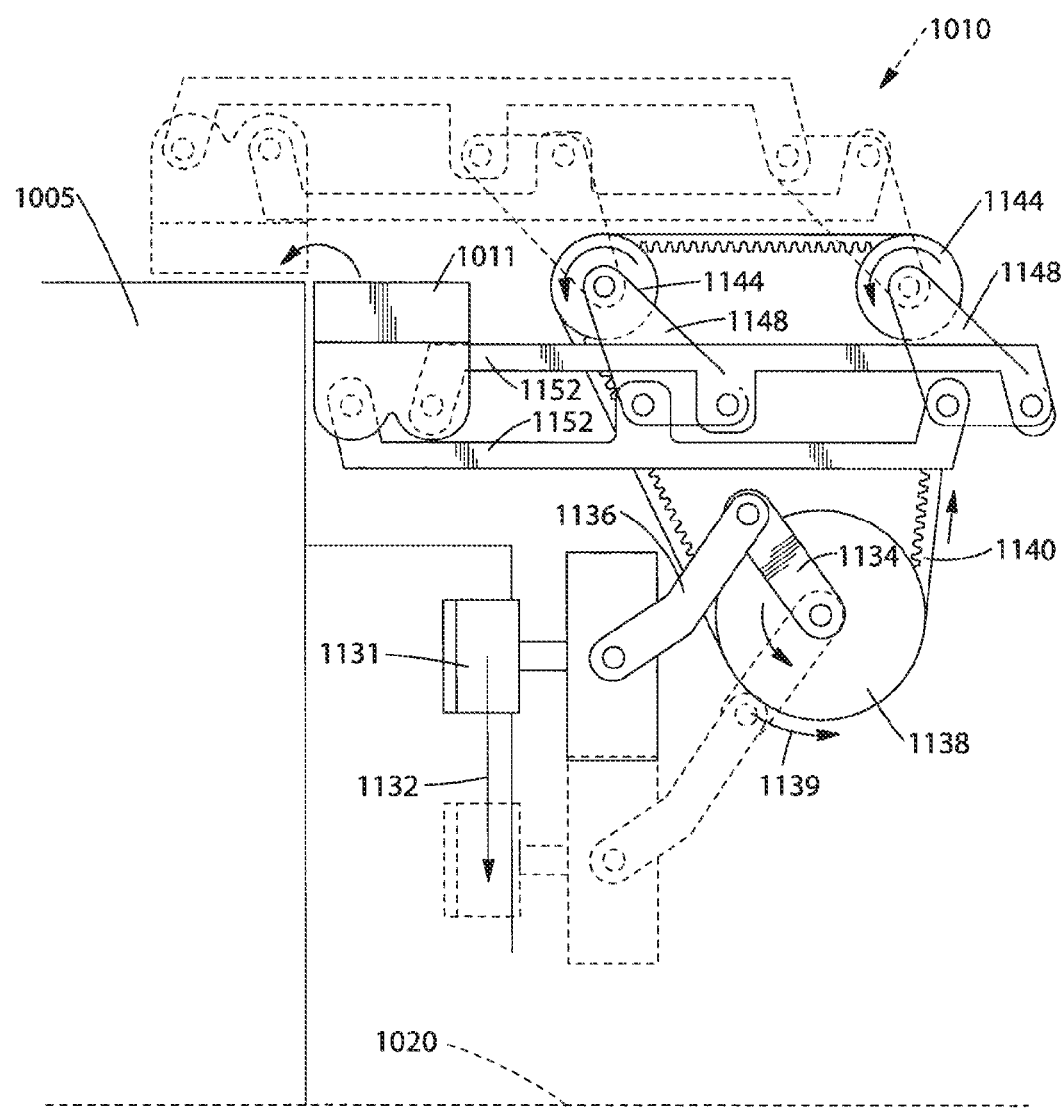
FIG. 12B shows an exemplary embodiment of a flipping mechanism contained in the folding apparatus of FIG. 12A.

Referring now to FIGS. 12A and 12B, an exemplary embodiment of a folding rotary drum 1000 which is capable of high-speed folding is shown. Folding rotary drum 1000 has a drum surface 1005 and a flipping mechanism 1010. Flipping mechanism 1010 has a folding portion 1011 which is not attached to drum surface 1005 and is supported in a rotatable position by use of linkages that are operatively linked to cam follower 1131. For example, primary linkage 1134 is operatively attached by a suitable pivot arm 1136 to the cam follower 1131, relative to an axis 1020. Upon rotation of the drum 1000 around axis 1020, the cam follower 1131 moves in a direction as indicated by arrow 1132. The radial motion of cam follower 1131 inwardly with respect to axis 1020, initiates the folding motion of the folding portion 1011. More specifically, as the cam follower 1131 moves, linkage 1134 rotates belt drive 1138 to rotate in the direction as indicated by arrow 1139. Belt drive 1138 moves a belt 1140 which thereby turns at least one drive roller 1144, which turns an associated linkage connector 1148, which itself is operatively connected to linkage 1152 which comprises a cooperating pair of links that are configured to facilitate a 180 degree fold-over motion of folding portion 1011. Other supporting links, shafts, bearings, and the like, which are not necessarily shown, can be configured in known ways to complete this linkage. It may be preferable to design the belt drive 1138 to have a diameter exactly twice the diameter of drive roller 1144, such that as belt drive 1138 rotates through an arc of 90 degrees, drive roller 1144 rotates through 180 degrees.

Figure 13A:
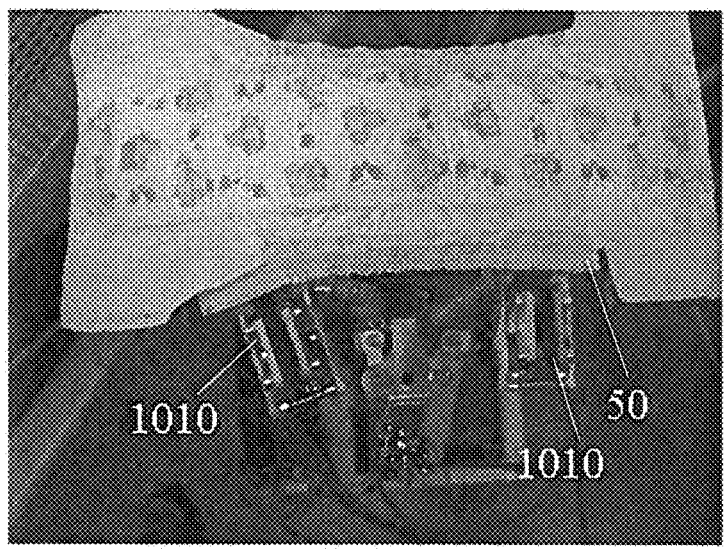
Figure 13B:
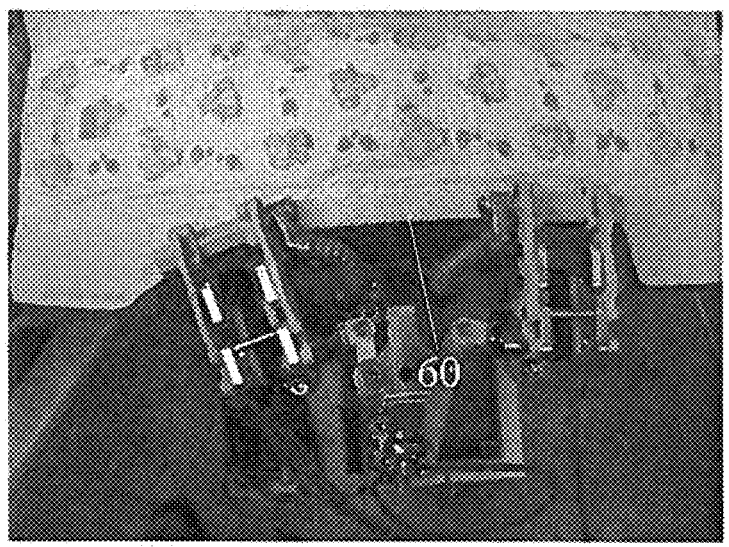
Figure 13C:
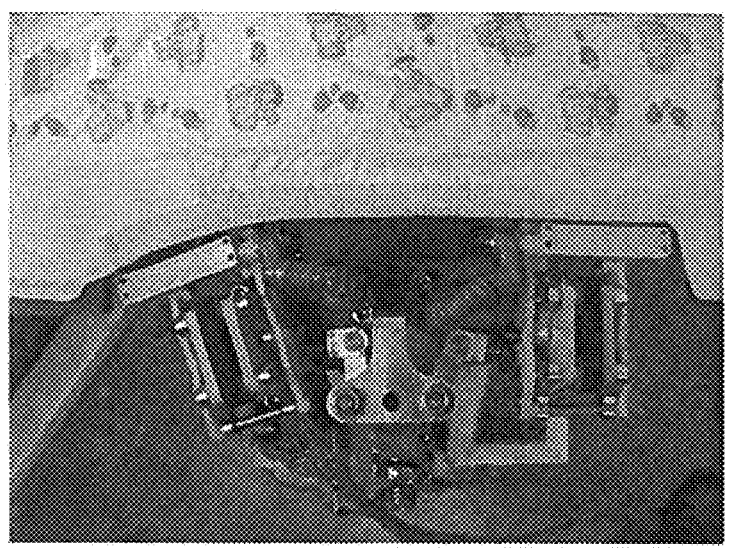

FIGS. 13A-C show an exemplary progression of the folding step. More specifically, FIG. 13A shows the longitudinal edge being held by folding portion 1011 in a pre-folded state. FIG. 13B shows the folding portion 1011 folding longitudinal edge upward and onto backsheet 26 to then create edge fold 60. FIG. 13C shows the folding portion 1011 releasing the newly-formed edge fold 60. Additional detail and teaching of similar folding apparatuses may be found in commonly assigned U.S. patent application Ser. No. 10/262,459, which is hereby incorporated by reference.

Figure 14:
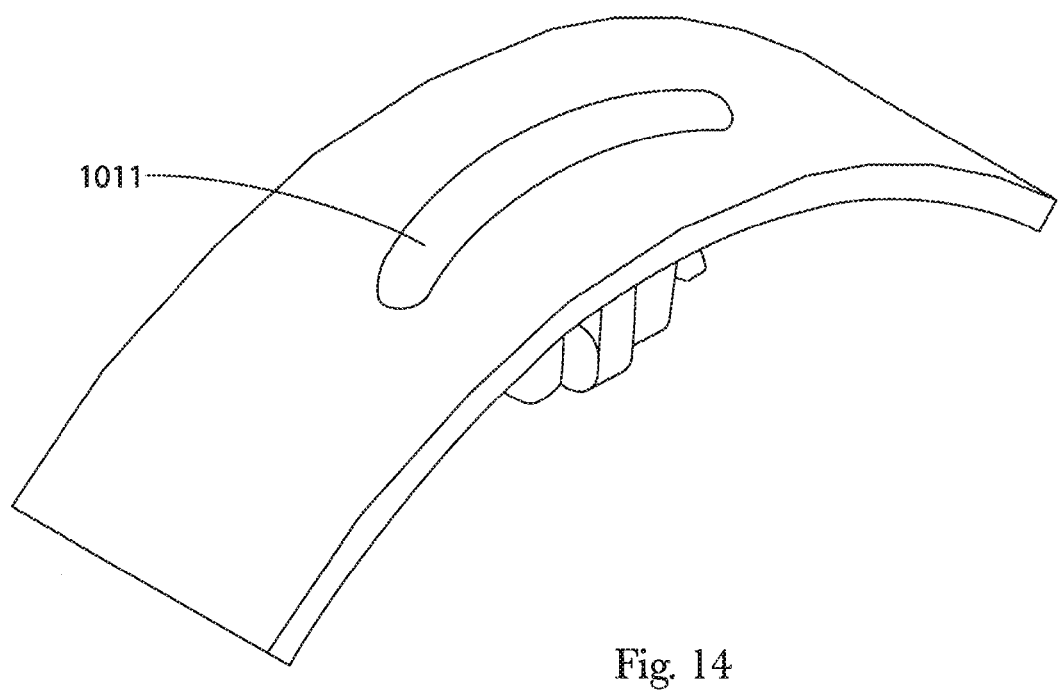
FIG. 14 shows an adaptation to the folding apparatus, wherein, the folding portion of FIGS. 13A-C are replaced with a curved folding member.

FIG. 14 shows an adaptation to folding apparatus 1000, wherein, the linear folding portion 1011 is replaced with a curved folding member 1011. Curved folding member 1011 is capable of making a non-linear edge fold 60 as exampled in FIGS. 5 and 6.

Figure 15A:
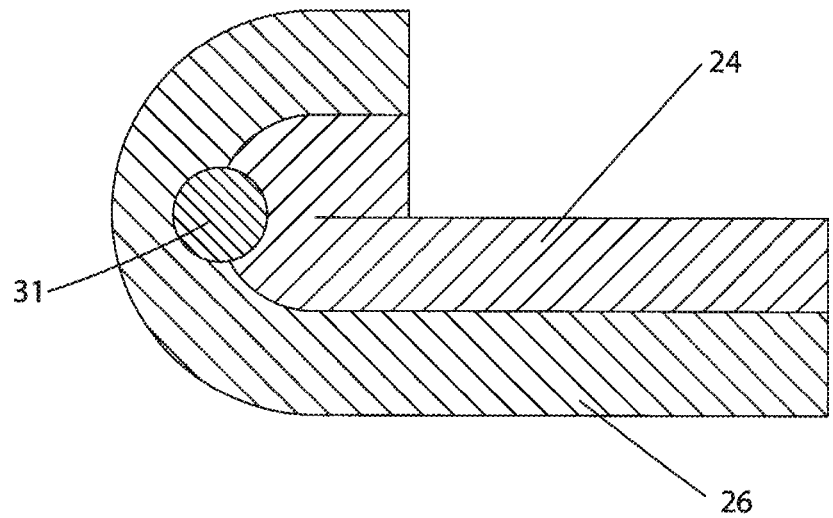
FIG. 15A shows a schematic view of an exemplary edge fold which is folded onto the topsheet.
Figure 15B:
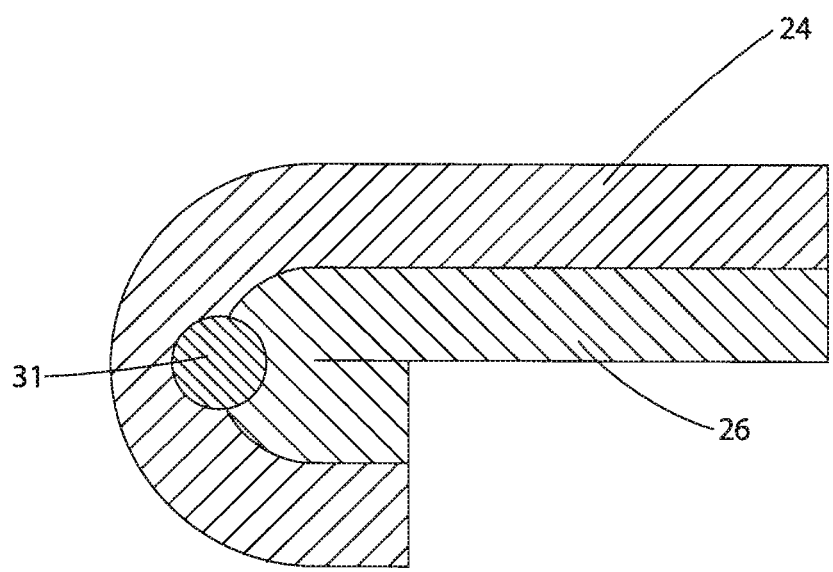
FIG. 15B shows a schematic view of an exemplary edge fold which is folded onto the backsheet.

FIGS. 15A and 15B show schematic views of exemplary edge folds 60. More particularly, FIG. 15A shows an edge fold 60, wherein, the fold is made back onto the topsheet 24 (i.e., inside fold). FIG. 15B shows an edge fold 60, wherein, the fold is made back onto the backsheet 26 (i.e., outside fold). While both types of folds are acceptable, it may be desirable to perform the inside fold because the terminal ends of the top sheet 24 and backsheet 26 are not visible during wearing.

Figure 15C:
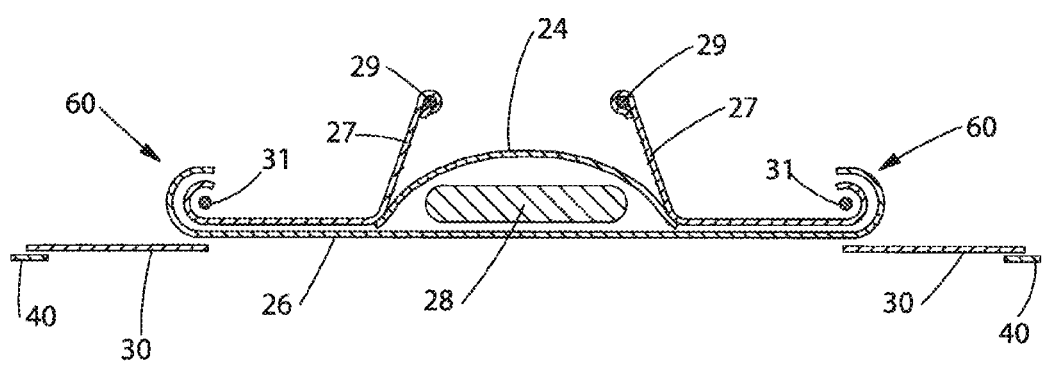
FIG. 15C shows a schematic view of an exemplary edge fold which is folded onto the barrier leg cuff; this example being a multi-piece chassis.

FIG. 15C shows a schematic view of an exemplary edge fold 60, wherein, the backsheet 26 and barrier leg cuff 27 together are folded back onto the barrier leg cuff 27. The chassis 22 in this particular example is a multi-piece chassis.

Figure 15D:
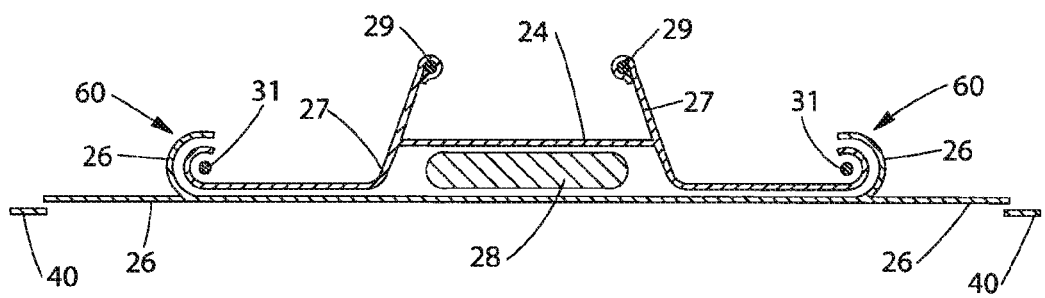
FIG. 15D shows a schematic view of an exemplary edge fold which is folded onto the barrier leg cuff; this example being a uni-body chassis.

FIG. 15D shows a schematic view of an exemplary edge fold 60, wherein, the backsheet 26 and barrier leg cuff 27 together are folded back onto the barrier leg cuff 27. The chassis 22 in this particular example is a uni-body chassis.

Figure 15E:
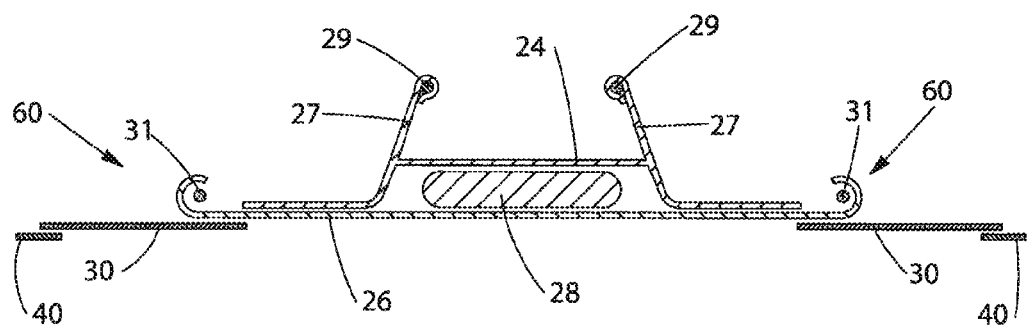
FIG. 15E shows a schematic view of an exemplary edge fold, wherein, the backsheet is folded onto itself as an inside fold; this example being a multi-piece chassis.
Figure 15F:
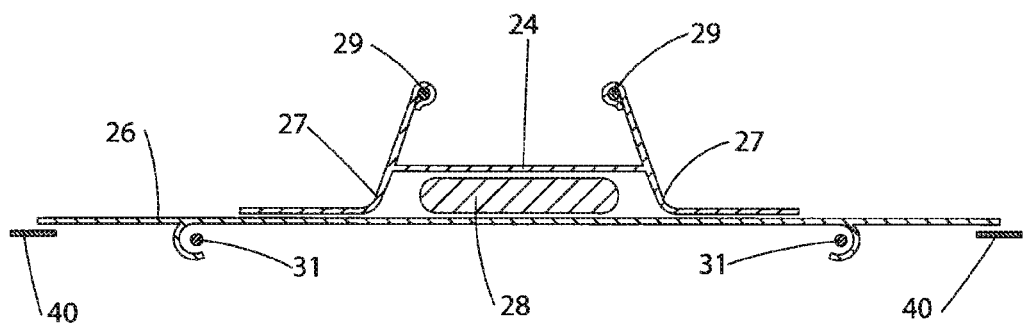
FIG. 15F shows a schematic view of an exemplary edge fold, wherein, the backsheet is folded onto itself as an outside fold; this example being a uni-body chassis.

FIG. 15E shows a schematic view of an exemplary edge fold 60, wherein, wherein, the backsheet 26 is folded onto itself as an inside fold. The chassis 22 in this particular example is a multi-piece chassis, although a uni-body chassis may also be contemplated.

FIG. 15E shows a schematic view of an exemplary edge fold 60, wherein, wherein, the backsheet 26 is folded onto itself as an outside fold. The chassis 22 in this particular example is a uni-body chassis, although a multi-piece chassis may also be contemplated.

Bonding

In yet another step of forming edge fold 60, the activated and folded chassis is bonded. Bonding of the folded portion to the chassis may be accomplished by application of adhesive, ultrasonic bonding, compression bonding, thermal bonding, radio frequency bonding, infrared bonding, combinations thereof, and any other suitable bonding means known in the art which is appropriate for the specific materials employed. Referring to FIGS. 2D-8D, a bond 68 is shown and provided inboard to leg elastic 31. For clarity, in FIGS. 2D-8D, layer(s) of material superjacent to the elastic 31 are illustrated as transparent.

Order of Steps

Figure 16:
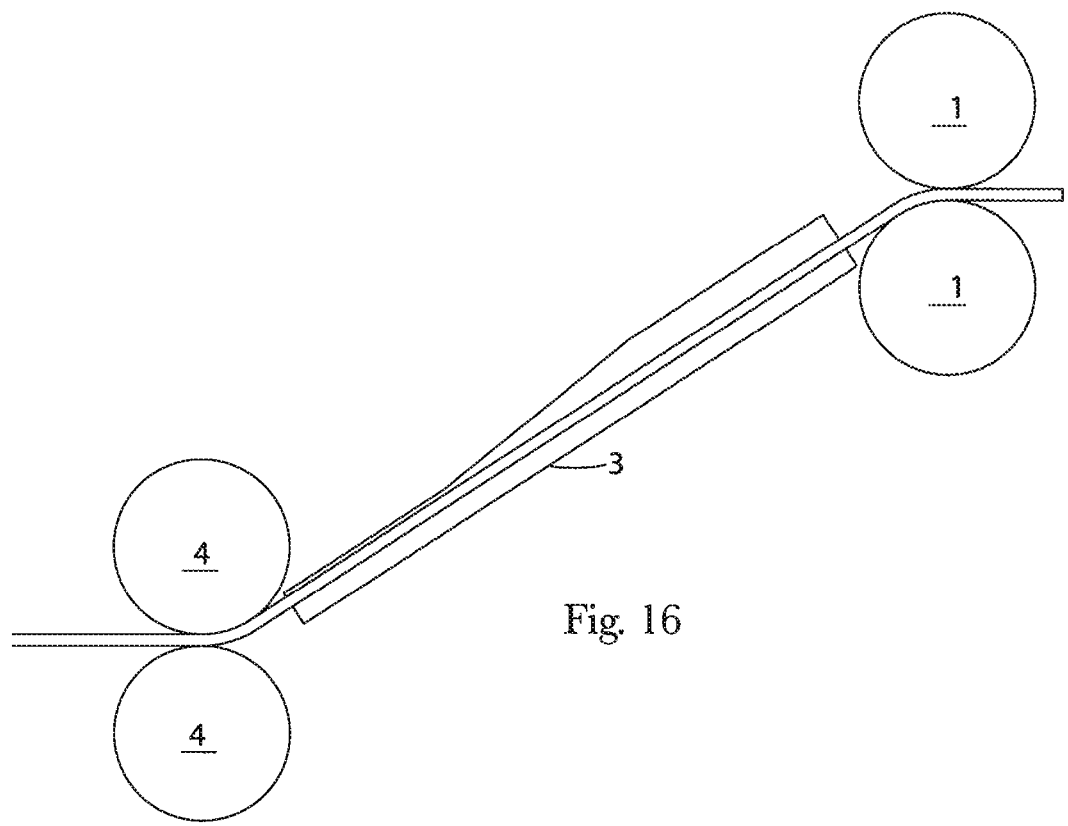
FIG. 16 shows a schematic view of the folding manufacturing process for making the embodiment of FIG. 2.

FIG. 16 shows an exemplary schematic view of the folding manufacturing process for making the embodiment of FIG. 2, wherein, the steps of activation 1 (in the machine direction), passive folding 3 (e.g., by way of a folding board) and bonding 4 (e.g., by way of compression rolls) are used.

Figure 17:
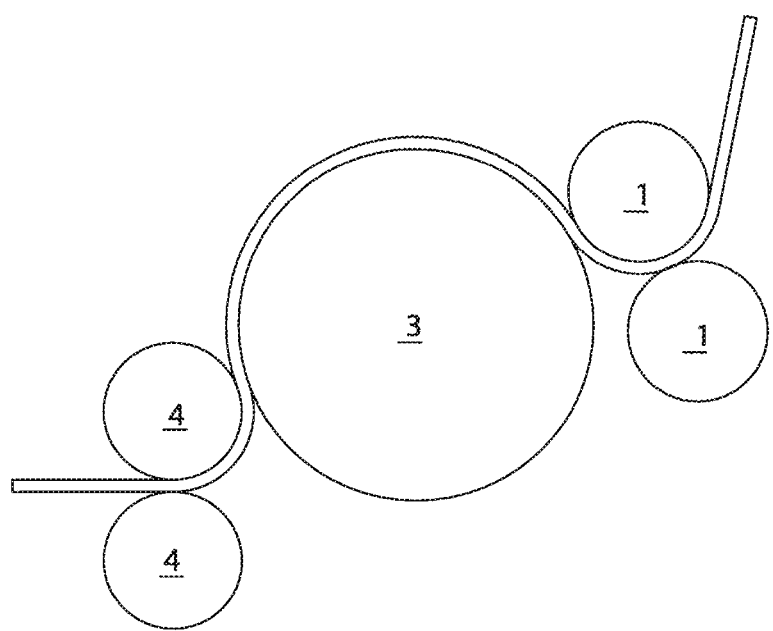
FIG. 17 shows a schematic view of the folding manufacturing process for making the embodiments of FIGS. 3 and 5.

FIG. 17 shows an exemplary schematic view of the folding manufacturing process for making the embodiments of FIGS. 3 and 5, wherein, the steps of activation 1 (in the machine direction), active folding 3 (e.g., by way of a folding rotary drum 1000) and bonding 4 (e.g., by way of compression rolls) are used.

Figure 18:
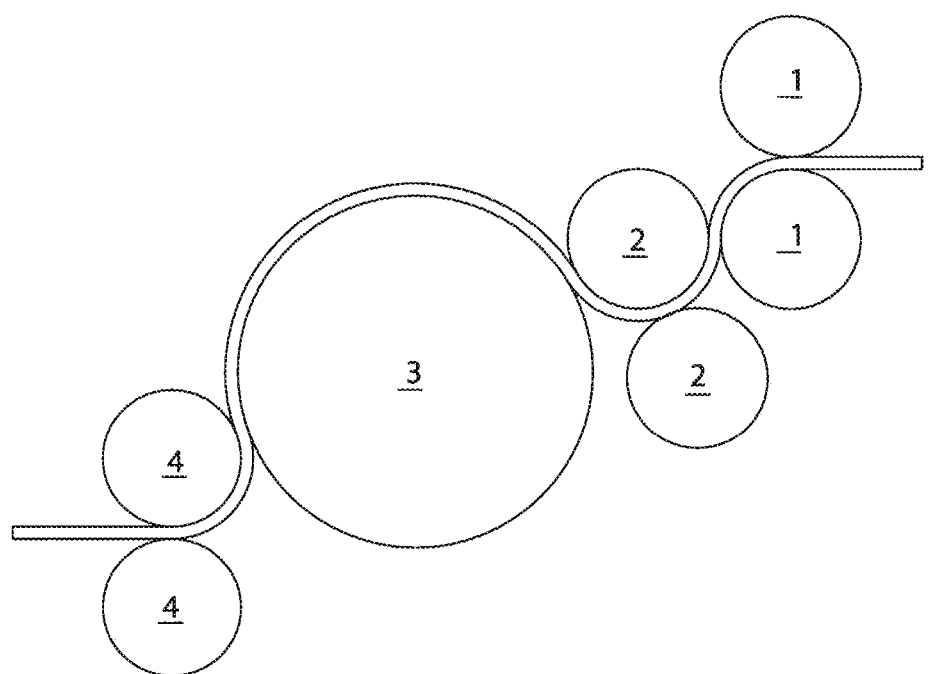
FIG. 18 shows a schematic view of the folding manufacturing process for making the embodiments of FIGS. 4 and 6-8.

FIG. 18 shows an exemplary schematic view of the folding manufacturing process for making the embodiments of FIGS. 4 and 6-8, wherein, the steps of activation 1 (in the machine direction), cutting 2 (e.g., by way of die cutting rolls to notch and/or shape), active folding 3 (e.g., by way of a folding rotary drum 1000) and bonding 4 (e.g., by way of compression rolls) are used.

While the order of the steps discussed herein were presented as activating, cutting, folding and bonding, the present invention is not limited to said order. For example, the activation step may be performed before or after the folding step, and before or after the bonding step. In fact, as discussed supra, the cutting step may even be eliminated.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be apparent to those skilled in the art that various other combinations and modifications can be made without departing from the scope of the invention. It is therefore intended to cover in the appended claims all such combinations and modifications that are within the scope of this invention.

What is claimed is:

1. An absorbent article comprising:
   a leg elastic; and
   a chassis with a longitudinal edge that includes a leg opening portion with a leg opening portion length, wherein:
   at least a portion of the chassis adjacent to the leg opening portion is an activated portion, which is incrementally stretched along an activated portion length, wherein the activated portion has an overall shape that is substantially arched;
   the leg elastic is disposed along at least a portion of the activated portion;
   at least a portion of the activated portion is a folded portion, folded transversely inward, along a folded portion length; and
   at least a portion of the folded portion is bonded along a bonded portion length and inboard to the leg elastic, forming an edge fold with substantially uniform gathers, wherein the portion of the leg elastic longitudinally coincident with the folded portion is disposed transversely outboard of the bonded portion and at or transversely inboard of the edge fold.

2. The absorbent article of claim 1, wherein the leg opening portion is substantially parallel to a longitudinal centerline of the article.

3. The absorbent article of claim 1, wherein substantially all of the leg opening portion is curved.

4. The absorbent article of claim 1, wherein the chassis includes a first waist region and a second waist region and the leg opening portion extends over substantially all of a distance between the first waist region and the second waist region.

5. The absorbent article of claim 1, wherein the activated portion extends over substantially all of the leg opening portion length.

6. The absorbent article of claim 1, wherein the folded portion extends along substantially all of the activated portion length.

7. The absorbent article of claim 1, wherein the bonded portion extends along substantially all of the folded portion length.

8. The absorbent article of claim 1, wherein the edge fold has an overall shape that is substantially curved.

9. The absorbent article of claim 1 wherein the bond is selected from the group including an adhesive bond, an ultrasonic bond, a compression bond, a thermal bond, a radio frequency bond, an infrared bond and combinations thereof.

10. The absorbent article of claim 1 wherein the absorbent article is disposable.

11. The absorbent article of claim 10 wherein the absorbent article is wearable.

12. The absorbent article of claim 1 wherein the absorbent article is selected from the group including disposable diapers, sanitary napkins, pantiliners, incontinence briefs, and incontinence undergarments.

13. The absorbent article of claim 1, further comprising a barrier leg cuff.

* * * * *